(12) United States Patent
Baulcombe et al.

(10) Patent No.: US 6,635,805 B1
(45) Date of Patent: Oct. 21, 2003

(54) METHODS AND DNA CONSTRUCTS FOR GENE SILENCING IN TRANSGENIC PLANTS

(75) Inventors: David Charles Baulcombe, Norwich (GB); Susan Mary Angell, Norwich (GB)

(73) Assignee: Plant Bioscience Limited, Norwich (GB)

( * ) Notice: Subject to any disclaimer, the term of this patent is extended or adjusted under 35 U.S.C. 154(b) by 0 days.

(21) Appl. No.: 09/367,117

(22) PCT Filed: Feb. 12, 1998

(86) PCT No.: PCT/GB98/00442

§ 371 (c)(1),
(2), (4) Date: Nov. 10, 1999

(87) PCT Pub. No.: WO98/36083

PCT Pub. Date: Aug. 20, 1998

(30) Foreign Application Priority Data

Feb. 14, 1997 (GB) .............................................. 9703146
Feb. 12, 1998 (GB) .............................................. 9800442

(51) Int. Cl.$^7$ ......................... C12N 15/82; C12N 15/84; C12N 15/90; C12N 5/04; A01H 5/00

(52) U.S. Cl. .................... 800/285; 435/320.1; 435/419; 435/468; 800/280; 800/288; 800/298

(58) Field of Search .............................. 435/69.1, 320.1, 435/410.412, 415–417, 419, 468, 469, 471; 800/278–280, 285–288, 294, 295, 282, 290, 283, 298, 301, 320–320.3, 305, 309, 312, 314, 317

(56) References Cited

U.S. PATENT DOCUMENTS 5,391,725 A  * 2/1995 Coruzzi et al. ............. 536/24.1
6,077,992 A    6/2000 Yadav ........................ 800/278

FOREIGN PATENT DOCUMENTS

| EP | 0194809 A1 | 9/1986 | ............ C12N/15/00 |
|---|---|---|---|
| EP | 0223452 A2 | 5/1987 | ............ C12N/15/00 |
| EP | 0425004 A2 | 5/1991 | ............ C12N/15/40 |
| WO | WO 88/10315 | 12/1988 | ............ C12Q/1/68 |
| WO | 9113994 | 9/1991 | ............ C12N/15/83 |
| WO | 9303161 | 2/1993 | ............ C12N/15/83 |
| WO | 9525801 | 9/1995 | ............ C12N/15/83 |
| WO | 9534668 | 12/1995 | ............ C12N/15/83 |
| WO | 9702352 | 1/1997 | ............ C12N/15/82 |

OTHER PUBLICATIONS

Ishihama et al, "Molecular anatomy of viral RNA–directed RNA polymerases", 1994, Arch Virol vol. 134 pp. 235–258.*
Timmermans et al "Geminiviruses and their uses as extra-chromosomal Replicons", 1994, Annu. Rev. Plant Physiol vol. 45 pp. 79–112.*
Thompson et al, "Coat protein of cauliflower mosaic virus binds to ssDNA", 1993, Journal of General Virology vol. 74 pp. 1141–1148.*
Flavell, "Inactivation of gene expression in plants as a consequence of specific sequence duplication", 1994, Proc. Natl. Acad. Sci. vol. 91, pp. 3490–3496.*
LewiN, Genes IV, 1990 pp. 124–125.*
Marathe et al, "RNA viruses as inducers, suppressors and target of post–transcriptional gene silence", 2000, Plant Molecular Biology vol. 43 pp. 295–306.*
Howard et al, "Breaking and Entering: Host Penetration by the fungal rice blast pathogen Magnaporthe grisea", 1996, Annu. Rev. Microbiol. vol. 50 pp. 491–512.*
Baulcombe et al, "Jellyfish green fluorescent protein as a reporter for virus infections", 1995, The Plant Journal vol. 7(6) pp. 1045–1053.*
Mueller et al, "Homology–dependent resistance: transgenic virus resistance in plants related to homology–dependent gene silencing", 1995 The Plant Journal vol. 7(6) pp 1001–1013.*
Kay et al, "Duplication of CaMV 35S Promoter Sequences Creates a Strong Enhancer for Plant Genes", 1987, Science vol. 236 pp1299–1302.*
Olivier Voinnet, RNA silencing as a plant immune system against viruses, Trends in Genetics, vol. 17, No. 8, Aug. 2001, pp. 449–459.*
Greg M. Arndt et al., Colocalization of antisense RNAs and ribozymes with their target mRNAs, Genome, 1997, vol. 40, pp. 785–797.*
S. M. Angell, et al. XP–002067897, Consistent gene silencing in transgenic plants expressing a replicating potato virus X RNA—The EMBO Journal vol. 16 No. 12 pp. 3675–3684, 1997.
D. C. Baulcombe, et al. XP–002067898. Ectopic pairing of homologous DNA and post–transcriptional gene silencing in transgenic plants—Current opinion in Biotechnology 1996, 1617:173–180.

(List continued on next page.)

Primary Examiner—Ashwin Mehta
(74) Attorney, Agent, or Firm—Dann, Dorfman, Herrell and Skillman

(57) ABSTRACT

The invention presents DNA constructs comprising a promoter operably linked to DNA which can be transcribed in a plant cell to an RNA transcript, wherein the RNA transcript comprises plant virus sequence from an RNA virus which confers on the RNA transcript the ability to replicate in the cytoplasm of the plant cell, wherein the transcript lacks all or part of the viral genome not required for replication in the cytoplasm, and further comprises at least one targeting sequence which is foreign to the plant virus sequence and causes post-transcriptional gene silencing of one or more target genes. The invention also presents methods to use the DNA construct to cause post-transcriptional gene silencing of a target gene in a plant.

19 Claims, 9 Drawing Sheets

OTHER PUBLICATIONS

John A. Lindbo, et al. XP–002067899, Induction of a Highly Specific Antiviral State in Transgenic Plants: Implications for Regulation of Gene Expression and Virus Resistance The Plant Cell, vol. 5, 1749–1759, Dec. 1993 © 1993 American Society of Plant Physiologists.

Jean Finnegan, et al. XP 002043134, Tansgene Inactivation: Plants Fight Back! Bio/Technology vol. 12 Sep. 1994.

Kook–Hyung Kim, et al. Mutations That Alter a Conserved Element Upstream of the Potato Virus X Triple Block and Coat Protein Genes Affect Subgenomic RNA Accumulation—Virology 232, 187–197 (1997) Article No. VY978565.

* cited by examiner

Northern analysis of RNA extracted from 35S/GUS scions 5 weeks post grafting

METHODS AND DNA CONSTRUCTS FOR GENE SILENCING IN TRANSGENIC PLANTS

This application is a §371 application of PCT/GB98/00442 filed Feb. 12, 1998 which in turns claims priority to GB applications 980042 and 9703146.2 filed Feb. 12, 1998 and Feb. 14, 1997 respectively.

FIELD OF THE INVENTION

The present invention relates to "gene silencing" ("gs") in transgenic plants. It employs "amplicon constructs", providing in various aspects nucleic acid molecules and vectors, cells and plants containing these, and methods and uses.

BACKGROUND OF THE INVENTION

"Gene silencing" is a term generally used to refer to suppression of expression of a gene. The degree of reduction may be so as to totally abolish production of the encoded gene product, but more usually the abolition of expression is partial, with some degree of expression remaining. The term should not therefore be taken to require complete "silencing" of expression. It is used herein where convenient because those skilled in the art well understand this.

Transgenes may be used to suppress endogenous plant genes. This was discovered originally when chalcone synthase transgenes in petunia caused suppression of the endogenous chalcone synthase genes (29,35). Subsequently it has been described how many, if not all plant genes can be "silenced" by transgenes (11,12,16,17,19,23). Gene silencing requires sequence similarity between the transgene and the gene that becomes silenced (Matzke, M. A. and Matzke, A. J. M. (1995), *Trends in Genetics*, 11: 1–3). This sequence homology may involve promoter regions or coding regions of the silenced gene (Matzke, M. A. and Matzke, A. J. M. (1993) *Annu. Rev. Plant Physiol. Plant Mol. Biol.*, 44: 53–76, Vaucheret, H. (1993) *C. R. Acad. Sci. Paris*, 316: 1471–1483, Vaucheret, H. (1994), *C. R. Acad. Sci. Paris*, 317: 310–323, Baulcombe, D. C. and English, J. J. (1996), Current Opinion In Biotechnology, 7: 173–180, Park, Y-D., et al (1996), *Plant J.*, 9: 183–194). When coding regions are involved the transgene able to cause gene silencing may have been constructed with a promoter that would transcribe either the sense or the antisense orientation of the coding sequence RNA. In at least one example the coding sequence transgene was constructed without a promoter (Van Blokland, R., et al (1994), *Plant J.*, 6: 861–877). It is likely that the various examples of gene silencing involve different mechanisms that are not well understood. In different examples there may be transcriptional or post transcriptional gs (3,4,10,24).

It has also become clear that gene silencing can account for some characteristics of transgenic plants that are not easily reconciled with conventional understanding of genetics. For example the wide variation in transgene expression between sibling lines with a transgene construct is due in part to gene silencing: low expressers are those with a high level of gene silencing whereas high expressers are those in which gene silencing is absent or induced late in plant development (10,13,14). Similarly gene silencing can often explain virus resistance in transgenic lines in which a viral cDNA transgene is expressed at a low level: the gene silencing mechanism acting on RNA inhibits accumulation of both the transgene RNA and the viral RNA (5,10,22).

In principle there is an enormous practical potential of gs for crop improvement. It is possible to silence genes conferring unwanted traits in the plant by transformation with transgene constructs containing elements of these genes. Examples of this type of application include gs of ripening specific genes in tomato to improve processing and handling characteristics of the harvested fruit; gs of genes involved in pollen formation so that breeders can reproducibly generate male sterile plants for the production of F1 hybrids; gs of genes involved in lignin biosynthesis to facilitate paper making from vegetative tissue of the plant; gs of genes involved in flower pigment production to produce novel flower colours; gs of genes involved in regulatory pathways controlling development or environmental responses to produce plants with novel growth habit or (for example) disease resistance; elimination of toxic secondary metabolites by gs of genes required for toxin production. In addition, gs is can be useful as a means of developing virus resistant plants when the transgene is similar to a viral genome.

A major complication in the practical exploitation of this phenomenon to date is the unpredictable and low occurrence of gs. Typically there will be strong gs in as few as 5–20% of lines generated with any one construct (for examples see (28,34)). Therefore, it has not been realistic to attempt gs in plants that are difficult to transform and for which it is difficult to produce many transformants. Similarly, it would be difficult to activate gs against several different traits or against several viruses in the same plant. Even with plants that are easy to transform the need to generate multiple lines limits the ease of exploitation of gs.

The first indication that an inoculated virus could elicit gene silencing was with transgenic plants in which the transgene included cDNA of tobacco etch potyvirus (22). The lines that exhibited this virus-induced gene silencing were initially high level expressers of the transgene. After inoculation with a strain of tobacco etch potyvirus that was identical or highly similar to the transgene there was a reduction in the amount of the transgene RNA and suppression of the originally inoculated virus in the upper leaves of the plant. These upper leaves were described as having recovered because they were virus and symptom free. They were also resistant against a secondary challenge inoculation with virus that was highly similar to the transgene at the nucleotide level. All of these effects are probably due to gs at the post transcriptional level.

However, there is nothing in this report to indicate that virus-induced gene silencing is intrinsically more reproducible than any other type of gene silencing. In fact there were some lines that displayed the virus-induced gene silencing and other lines that did not (22). Furthermore there are many reports that refer to virus inoculation of transgenic plants carrying transgenes that are similar or identical to the inoculated virus. Of these reports only a minority describe virus-induced gene silencing. Thus with viral transgenes the virus induced gene silencing is the exception rather than the rule. That is, as indicated above, there was no indication from this work that gene silencing by inoculated viruses is intrinsically reproducible.

Biosource Technologies, Inc. (20,21) have suggested the use of genetic constructions based on RNA viruses which replicate in the cytoplasm of cells to provide inhibitory RNA, either anti-sense or co-suppressor RNA. Cells are transfected with the cytoplasmically-replicating genetic constructions in which the RNA encoding region is specific for the gene of interest. Experimental evidence illustrating the drawbacks and limitations of the Biosource approach is included below.

SUMMARY OF THE INVENTION

The present invention aims to overcome one or more of the many problems in the art. For instance, experimental evidence included below demonstrates with embodiments of the present invention gs is achievable more reproducibly than with conventional technology.

Briefly, the present invention in various aspects makes use of an amplicon construct which will exhibit gs targeted against sequence with homology to a sequence within the amplicon. An amplicon is a transgene DNA construct including a promoter and cDNA of at least part of a viral genome, and optionally a transcriptional terminator. Preferably, the construct includes a "targeting sequence", which may be a sequence foreign to the virus, for specifically targeting down-regulation of a gene of interest ("target gene"). Further details are discussed below.

Incorporation of a construct in the genome of transgenic plants in accordance with the present invention may be used to ensure the viral cDNA is transcribed from the promoter in many or most cells of the plant, though use of a tissue- or developmentally-regulated and/or inducible promoter is possible. If the viral cis-acting elements and trans-acting factors necessary for replication are intact there will be replication of the viral RNA in the transgenic plant. As a consequence, either direct or indirect, there will be activation of gs targeted against sequences with sufficient homology to a sequence included with the replicating viral RNA, the "targeting sequence".

An amplicon construct may have an unmodified viral cDNA. In such a case the plant may be resistant against the virus as a result of gs. Other amplicon constructs may have a foreign targeting sequence inserted into the viral cDNA and the gs will be targeted against the corresponding sequence as well as against the virus. The targeting sequence may be part of a different viral genome, in which case the plant may also be resistant against this second virus. The targeting sequence may be derived from a nuclear gene or transgene, or a gene on an extrachromosomal element such as a plasmid, and the gs targeted against that gene and homologues.

The present invention will now be discussed in more detail.

According to one aspect of the present invention there is provided, preferably within a vector suitable for stable transformation of a plant cell, a DNA construct in which a promoter is operably linked to DNA for transcription in a plant cell of an RNA molecule which includes plant virus sequences which confer on the RNA molecule the ability to replicate in the cytoplasm of a plant cell following transcription. The RNA transcribed from the DNA which is under the transcriptional control of the promoter is capable of replication in the cytoplasm of a plant cell by virtue of including appropriate plant virus sequences. The transcripts, possibly including a sequence foreign to the virus, replicate as if they are viral RNAs, activating gs.

The transcribed RNA generally includes a sequence ("targeting sequence") which is complementary to a sequence in a target gene, either in the sense or anti-sense orientation, or a sequence which has sufficient homology to a target sequence for down-regulation of expression of the target gene to occur. Whilst not to be bound by any theory, it is believed that sense and anti-sense regulation involve hybridisation between sequences which are sufficiently complementary to hybridise under conditions within a cell.

The targeting sequence within the construct may be foreign to the plant virus, i.e. of or derived from a gene or sequence which the virus lacks. Those skilled in the art will understand that terms such as "exogenous" or "heterologous" may equally be used in this context.

A vector which contains the construct may be used in transformation of one or more plant cells to introduce the construct stably into the genome, so that it is stably inherited from one generation to the next. This is preferably followed by regeneration of a plant from such cells to produce a transgenic plant.

Thus, in further aspects, the present invention also provides the use of the construct or vector in production of a transgenic plant, methods of transformation of cells and plants, plant and microbial (particularly Agrobacterium) cells, and various plant products.

The function of the promoter in the amplicon construct is to ensure that the DNA is transcribed into RNA containing the viral sequences. By "promoter" is meant a sequence of nucleotides from which transcription may be initiated of DNA operably linked downstream (i.e. in the 3' direction on the sense strand of double-stranded DNA). A promoter "drives" transcription of an operably linked sequence.

"Operably linked" means joined as part of the same nucleic acid molecule, suitably positioned and oriented for transcription to be initiated from the promoter. DNA operably linked to a promoter is "under transcriptional initiation regulation" of the promoter, or "in functional combination" therewith.

Preferred promoters may include the 35S promoter of cauliflower mosaic virus or the nopaline synthase promoter of *Agrobacterium tumefaciens* (Sanders, P. R., et al (1987), *Nucleic Acids Res*., 15: 1543–1558). These promoters are expressed in many, if not all, cell types of many plants. Other constitutively expressed promoters may be used effectively as components of amplicon construct producing gs. Depending on the target gene of amplicon gs, other promoters including those that are developmentally regulated or inducible may be used. For example, if it is necessary to silence the target gene specifically in a particular cell type the amplicon construct may be assembled with a promoter that drives transcription only in that cell type. Similarly, if the target gene is to be silenced following a defined external stimulus the amplicon construct may incorporate a promoter that is be activated specifically by that stimulus. Promoters that are both tissue specific and inducible by specific stimuli may be used.

Inducible promoters may be advantageous in certain circumstances because they place the timing of reduction in expression of the target gene of interest under the control of the user.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level which brings about the desired phenotype.

Suitable promoters include the Cauliflower Mosaic Virus 35S (CaMV 35S) gene promoter that is expressed at a high level in virtually all plant tissues (Benfey et al, 1990a and 1990b) and the maize glutathione-S-transferase isoform II (GST-II-27) gene promoter which is activated in response to application of exogenous safener (WO93/01294, ICI Ltd). The GST-II-27 gene promoter has been shown to be induced by certain chemical compounds which can be applied to growing plants. The promoter is functional in both monocotyledons and dicotyledons. It can therefore be used to control gene expression in a variety of genetically modified plants, including field crops such as canola, sunflower, tobacco, sugarbeet, cotton; cereals such as wheat, barley, rice, maize, sorghum; fruit such as tomatoes, mangoes, peaches, apples, pears, strawberries, bananas, and melons; and vegetables such as carrot, lettuce, cabbage and onion. The GST-II-27 promoter is also suitable for use in a variety of tissues, including roots, leaves, stems and reproductive tissues.

A construct for use in accordance with the present invention includes sequences which are DNA copies of cis-acting elements in the viral genome and of open reading frames in the viral genome that are required for replication of the viral RNA. They should be arranged in the amplicon construct so that the transcripts of the amplicon construct will replicate in the plant cells independently of other transgenes or of viruses inoculated to the plants. The cDNA copies of any other parts of the viral genome need not be included in the amplicon construct provided that their absence does not interfere with replication of the amplicon transcripts. An optional but important additional feature of some amplicon constructs in accordance with the present invention is the insertion of foreign sequences into the viral cDNA. The site of insertion of these foreign sequences is so that the foreign sequence is replicated, as RNA, as part of the viral RNA produced by transcription of the amplicon in a plant cell. The target of gene silencing is determined by the viral cDNA and any foreign targeting sequence in the amplicon construct.

DETAILED DESCRIPTION OF THE INVENTION

The amplicon constructs used in the experimental exemplification described in this application for the purpose of illustration of aspects of the present invention without limitation are based on cDNA of the potato virus X (PVX) genome (Kavanagh, T. A., et al (1992), *Virology*, 189: 609–617). Many, if not all, other RNA or DNA viruses of plants may be used in generation of amplicon constructs in a manner that is similar to that described here for PVX. Particularly suitable alternatives to PVX are those viruses for which it is known that foreign sequence is tolerated as part of the replicating viral genome. Included in these examples are tobacco mosaic virus (Dawson, W. O., et al (1989), *Virology*, 172: 285–292), tobacco etch virus (Dolja, V. V., et al (1992), *Proc. Natl. Acad. Sci. USA*, 89: 10208–10212), tobacco rattle virus (Ziegler-Graff, V., et al (1991), *Virology*, 182: 145–155), tomato bushy stunt virus (Scholthof, H. B., et al (1993), *Mol. Plant-Microbe Interact.*, 6: 309–322), brome mosaic virus (Mori, M., et al (1993), *J. Gen. Virol.*, 74: 1255–1260), cauliflower mosaic virus (Futterer, J. and Hohn, T. (1991), *EMBO J.*, 10: 3887–3896), african cassava mosaic virus (Ward, A., et al (1988), *EMBO J.*, 7: 1583–1587), tomato golden mosaic virus. Preferred viruses for use in the present invention may be RNA viruses.

A foreign targeting sequence may be included in the construct as a substitution for a viral gene or sequence that is not required for replication or as an additional sequence added to the viral genome. A foreign sequence may be included in the amplicon as an intact open reading frame and so that it is transcribed as a subgenomic RNA. However, a foreign sequence may be included anywhere in the viral cDNA irrespective of the location of subgenomic promoter.

A sequence foreign to the viral nucleic acid and homologous or similar to a target gene of interest, may be included in a sense or anti-sense orientation in the amplicon.

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) *Nature* 334, 724–726; Zhang et al, (1992) *The Plant Cell* 4, 1575–1588, English et al., (1996) *The Plant Cell* 8, 179–188. Antisense technology is also reviewed in Bourque, (1995), *Plant Science* 105, 125–149, and Flavell, (1994) *PNAS USA* 91, 3490–3496.

An alternative is to use a copy of all or part of the target gene inserted in sense, that is the same, orientation as the target gene, to achieve reduction in expression of the target gene by co-suppression. See, for example, van der Krol et al., (1990) *The Plant Cell* 2, 291–299; Napoli et al., (1990) *The Plant Cell* 2, 279–289; Zhang et al., (1992) *The Plant Cell* 4, 1575–1588, and U.S. Pat. No. 5,231,020.

The complete sequence corresponding to the coding sequence (in reverse orientation for anti-sense) need not be used. For example fragments of sufficient length may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A further possibility is to target a conserved sequence of a gene, e.g. a sequence that is characteristic of one or more genes in one or more pathogens against which resistance is desired, such as a regulatory sequence.

A foreign sequence may be 500 nucleotides or less, possibly about 400 nucleotides, about 300 nucleotides, about 200 nucleotides, or about 100 nucleotides. It may be possible to use oligonucleotides of much shorter lengths, 14–23 nucleotides, although longer fragments, and generally even longer than 500 nucleotides are preferable where possible.

It may be preferable that there is complete sequence identity in the targeting (e.g. foreign) sequence in the amplicon and the target sequence in the plant, though total complementarity or similarity of sequence is not essential. One or more nucleotides may differ in the targeting sequence from the target gene. Thus, a targeting sequence employed in a construct in accordance with the present invention may be a wild-type sequence (e.g. gene) selected from those available, or a mutant, derivative, variant or allele, by way of insertion, addition, deletion or substitution of one or more nucleotides, of such a sequence. A foreign sequence need not include an open reading frame or specify an RNA that would be translatable. As noted, a foreign sequence may be inserted into the amplicon construct in either orientation, for sense or anti-sense regulation. It may be preferred for there to be sufficient homology for the respective anti-sense and sense RNA molecules to hybridise. There may be gs even where there is about 5%, 10%, 15% or 20% or more mismatch between the targeting, e.g. foreign, sequence in the amplicon and the target gene.

In embodiments of the present invention which have been experimentally exemplified as described below for illustrative and non-limiting purposes only, the foreign sequence in the amplicon that determined the target of gene silencing was the uidA reporter gene (Jefferson, R. A., et al (1986), *Proc. Natl. Acad. Sci. USA*, 83: 8447–8451) or the gene encoding the jellyfish green fluorescent protein (Chalfie et al. (1994) *Science* 263: 802–805). Other disclosed example genes include tomato DWARF and arabidopsis phytoene desaturase. However, any other gene of plant, animal, fungal, bacterial or viral origin may be a target of amplicon gs provided that the corresponding foreign sequence is incorporated into the amplicon construct. Particularly suitable as targets are genes that have already been shown to be suppressible by gs in the literature. These may include, for example, chalcone synthase of petunia or polygalacturonase of tomato (Jorgensen, R. A. (1995), *Science*, 268: 686–691, Hamilton, A. J., et al (1995), Current Topics In i Microbiology and Immunology, 197: 77–89).

One or more targeting sequences may be included in the construct, to provide for suppression of one or more genes, e.g. when down-regulation of more than one gene is required at the same time, or for conferring resistance to more than one pathogen. A targeting sequence with sufficient homology to more than one target sequence may be used in suppressing more than one gene.

An additional optional feature of a construct used in accordance with the present invention is a transcriptional terminator. The transcriptional terminator from nopaline synthase gene of agrobacterium tumefaciens (Depicker, A., et al (1982), *J. Mol. Appl. Genet.*, 1: 561–573) may be used, and is experimentally exemplified below. Other suitable transcriptional terminators include but are not restricted to those from soybean actin, ribulose bisphosphate carboxylase of Nicotiana plumbaginifolia (Poulson, C., et al (1986), *Mol. Gen. Genet.*, 205: 193–200) and alpha amylase of wheat (Baulcombe, D. C., et al (1987), *Mol. Gen. Genet.*, 209: 33–40). A transcriptional terminator sequence foreign to the virus may not be included in a construct of the invention in particular when the viral sequences included in the construct include one or more transcriptional terminator sequences.

Those skilled in the art are well able to construct vectors and design protocols for recombinant gene expression. For further details see, for example, *Molecular Cloning: a Laboratory Manual*: 2nd edition, Sambrook et al, 1989, Cold Spring Harbor Laboratory Press.

Many known techniques and protocols for manipulation of nucleic acid, for example in preparation of nucleic acid constructs, mutagenesis, sequencing, introduction of DNA into cells and gene expression, and analysis of proteins, are described in detail in Protocols in *Molecular Biology*, Second edition, Ausubel et al. eds., John Wiley & Sons, 1992.

Specific procedures and vectors previously used with wide success upon plants are described by Bevan, Nucl. Acids Res. (1984) 12, 8711–8721), and Guerineau and Mullineaux, (1993) Plant transformation and expression vectors. In: Plant Molecular Biology Labfax (Croy RRD ed) Oxford, BIOS Scientific Publishers, pp 121–148.

For introduction into a plant cell, the nucleic acid construct may be in the form of a recombinant vector, for example an Agrobacterium binary vector. Microbial, particularly bacterial and especially Agrobacterium, host cells containing a construct according to the invention or a vector which includes such a construct, particularly a binary vector suitable for stable transformation of a plant cell, are also provided by the present invention.

Nucleic acid molecules, constructs and vectors according to the present invention may be provided isolated and/or purified (i.e. from their natural environment), in substantially pure or homogeneous form, or free or substantially free of other nucleic acid. Nucleic acid according to the present invention may be wholly or partially synthetic. The term "isolate" encompasses all these possibilities.

An aspect of the present invention is the use of a construct or vector according to the invention in the production of a transgenic plant.

A further aspect provides a method including introducing the construct or vector into a plant cell such that the construct is stably incorporated into the genome of the cell.

Any appropriate method of plant transformation may be used to generate plant cells containing a construct within the genome in accordance with the present invention. Following transformation, plants may be regenerated from transformed plant cells and tissue.

Successfully transformed cells and/or plants, i.e. with the construct incorporated into their genome, may be selected following introduction of the nucleic acid into plant cells, optionally followed by regeneration into a plant, e.g. using one or more marker genes such as antibiotic resistance. Selectable genetic markers may be used consisting of chimaeric genes that confer selectable phenotypes such as resistance to antibiotics such as kanamycin, hygromycin, phosphinotricin, chlorsulfuron, methotrexate, gentamycin, spectinomycin, imidazolinones and glyphosate.

When introducing a nucleic acid into a cell, certain considerations must be taken into account, well known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material should occur. Finally, as far as plants are concerned the target cell type must be such that cells can be regenerated into whole plants.

Plants transformed with the DNA segment containing the sequence may be produced by standard techniques which are already known for the genetic manipulation of plants. DNA can be transformed into plant cells using any suitable technology, such as a disarmed Ti-plasmid vector carried by Agrobacterium exploiting its natural gene transfer ability (EP-A-270355, EP-A-0116718, NAR 12(22) 8711–87215 1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614 Gelvin Debeyser—see attached) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d). Physical methods for the transformation of plant cells are reviewed in Oard, 1991, *Biotech. Adv.* 9: 1–11.

Agrobacterium transformation is widely used by those skilled in the art to transform dicotyledonous species. Recently, there has been substantial progress towards the routine production of stable, fertile transgenic plants in almost all economically relevant monocot plants (Toriyama, et al. (1988) *Bio/Technology* 6, 1072–1074; Zhang, et al. (1988) *Plant Cell Rep.* 7, 379–384; Zhang, et al. (1988) *Theor Appl Genet* 76, 835–840; Shimamoto, et al. (1989)

Nature 338, 274–276; Datta, et al. (1990) Bio/Technology 8, 736–740; Christou, et al. (1991) Bio/Technology 9, 957–962; Peng, et al. (1991) International Rice Research Institute, Manila, Philippines 563–574; Cao, et al. (1992) Plant Cell Rep. 11, 585–591; Li, et al. (1993) Plant Cell Rep. 12, 250–255; Rathore, et al. (1993) Plant Molecular Biology 21, 871–884; Fromm, et al. (1990) Bio/Technology 8, 833–839; Gordon-Kamm, et al. (1990) Plant Cell 2, 603–618; D'Halluin, et al. (1992) Plant Cell 4, 1495–1505; Walters, et al. (1992) Plant Molecular Biology 18, 189–200; Koziel, et al. (1993) Biotechnology 11, 194–200; Vasil, I. K. (1994) Plant Molecular Biology 25, 925–937; Weeks, et al. (1993) Plant Physiology 102, 1077–1084; Somers, et al. (1992) Bio/Technology 10, 1589–1594; WO92/14828). In particular, Agrobacterium mediated transformation is now emerging also as an highly efficient transformation method in monocots (Hiei et al. (1994) The Plant Journal 6, 271–282).

The generation of fertile transgenic plants has been achieved in the cereals rice, maize, wheat, oat, and barley (reviewed in Shimamoto, K. (1994) Current Opinion in Biotechnology 5, 158–162; Vasil, et al. (1992) Bio/Technology 10, 667–674; Vain et al., 1995, Biotechnology Advances 13 (4): 653–671; Vasil, 1996, Nature Biotechnology 14 page 702).

Microprojectile bombardment, electroporation and direct DNA uptake are preferred where Agrobacterium is inefficient or ineffective. Alternatively, a combination of different techniques may be employed to enhance the efficiency of the transformation process, eg bombardment with Agrobacterium coated microparticles (EP-A-486234) or microprojectile bombardment to induce wounding followed by co-cultivation with Agrobacterium (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewd in Vasil et al., Cell Culture and Somatic Cel Genetics of Plants, Vol I, II and III, Laboratory Procedures and Their Applications, Academic Press, 1984, and Weissbach and Weissbach, Methods for Plant Molecular Biology, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

Also according to the invention there is provided a plant cell having incorporated into its genome a DNA construct as disclosed. A further aspect of the present invention provides a method of making such a plant cell involving introduction of a vector including the construct into a plant cell. Such introduction should be followed by recombination between the vector and the plant cell genome to introduce the sequence of nucleotides into the genome. RNA encoded by the introduced nucleic acid construct may then be transcribed in the cell and descendants thereof, including cells in plants regenerated from transformed material. A gene stably incorporated into the genome of a plant is passed from generation to generation to descendants of the plant, so such decendants should show the desired phenotype.

The present invention also provides a plant comprising a plant cell as disclosed.

A plant according to the present invention may be one which does not breed true in one or more properties. Plant varieties may be excluded, particularly registrable plant varieties according to Plant Breeders' Rights. It is noted that a plant need not be considered a "plant variety" simply because it contains stably within its genome a transgene, introduced into a cell of the plant or an ancestor thereof.

In addition to a plant, the present invention provides any clone of such a plant, seed, selfed or hybrid progeny and descendants, and any part of any of these, such as cuttings, seed. The invention provides any plant propagule, that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, off-spring, clone or descendant. Plant extracts and derivatives are also provided.

The present invention may particularly be applied in plants such as natural hosts of a plant virus, including any mentioned herein, though it is an advantage of embodiments of the present invention that viruses may be used for gene silencing in plants which are not their natural hosts, as has been demonstrated experimentally and is described below. Indeed the present inventors have demonstrated that PVX, used in many of the Examples below, can replicate in monocots in addition to its natural hosts.

The present invention may be used in plants such as crop plants, including cereals and pulses, maize, wheat, potatoes, tapioca, rice, sorgum, millet, cassava, barley, pea and other root, tuber or seed crops. Important seed crops are oil seed rape, sugar beet, maize, sunflower, soybean and sorghum. Horticultural plants to which the present invention may be applied may include lettuce, endive and vegetable brassicas including cabbage, broccoli and cauliflower, and carnations and geraniums. The present invention may be applied to tobacco, cucurbits, carrot, strawberry, sunflower, tomato, pepper, chrysanthemum, poplar, eucalyptus and pine.

As noted, transcription from the construct in the genome of a plant cell yields a cytoplasmically-replicating RNA able to down-regulate expression of a target gene in the cell, which target gene may be of the plant, endogenous to the plant genome or a transgene, or of a pathogen such as a virus.

Thus, a further aspect of the present invention provides a method which includes causing or allowing transcription from a construct as disclosed within the genome of a plant cell.

A further aspect of the present invention provides a method of reducing or suppressing or lowering the level of expression of a gene of interest (or "target gene") in a plant cell, the method including causing or allowing transcription from a construct as disclosed. Transcription produces RNA and is generally followed by replication of the transcribed RNA by virtue of the inclusion of the viral sequence. The construct may include the target gene sequence or a fragment thereof in a sense or anti-sense orientation, or a sequence with sufficient homology to the target gene sequence or a fragment thereof for the level of expression of the target gene to be reduced on production of the RNA.

As demonstrated in the Examples hereinafter, in certain embodiments the target gene may be remote from the site of the amplicon replication, which may only be activated in certain cells (for instance because the amplicon is activated by an inducible promoter). In such cases the gs may be achieved through the demonstrated systemic or remote effect. In the light of the present work, it appears that this effect may be analogous to that disclosed in Voinnet & Baulcombe (1997) Nature 389: page 553, (although in that case the initiator of the systemic gs signal was not a cytoplasmically replicating construct). Thus the distal effect may be particularly effective when the amplicon is activated in a photosynthetic 'source' tissue, while the target tissue is present (either locally or systemically) in 'sink' tissue(s).

With respect to the level of expression of a gene of interest in a cell, the method will generally result in a decrease in the level of expression as compared with the level in the absence of the intervention, i.e. in comparison with equivalent wild-type cells, e.g. of plants of the same species. (Cells which are wild-type in respect of the level of expression of the gene of interest may of course not be wild-type in every respect.)

Where the target is a gene of a pathogen such as a virus, down-regulation of expression may provide an increase in resistance to the pathogen, particularly where the gene is required for, or is at least involved in, replication and/or infectivity (e.g. in an RNA-dependent RNA polymerase in a virus such as cowpea mosaic virus (Sijen, T., et al (1996), *Plant Cell*, 8: 2277–2294)).

The present invention will now be illustrated and exemplified with reference to experimental results and the accompanying figures. Further aspects and embodiments of the present invention, and modifications of those disclosed herein, will be apparent to those skilled in the art. All documents mentioned anywhere herein are incorporated by reference.

BRIEF DESCRIPTION OF THE DRAWINGS

FIG. 2 shows a time course of symptom expression on manually inoculated amplicon and non-transformed plants. Twenty plants from each amplicon line were manually inoculated with 0.5 μg of virion RNA. For each experiment, twenty non-transformed plants were also inoculated. The mean (+/−SE) percentage of plants showing symptoms at 5 to 14 days post inoculation are plotted. No symptoms were visible on any plant until 6 days post inoculation.

FIG. 3(a): Schematic representation of the pUC-based plasmid pSLJ4D4 (not drawn to scale). The GUS sequence was inserted between the 35S promoter and ocs terminator sequence. The unique BamHI site at the 3' end of the GUS ORF was used to insert each of the eight fragments of the PVX genome shown in FIG. 3(b).

FIG. 3(b): Schematic representation of the PVX genome. RdRp, RNA-dependent RNA polymerase; 25, 12, 8, the "triple gene block"; CP, coat protein gene. The bars below the diagram denote the regions of the genome separately cloned into the BamHI site of pSLJ4D4. The direction of the arrow heads indicate the sense or antisense orientation of the fragments in the BamHI site. The numbers adjacent to each bar denote the resulting plasmid clone. The size of the PVX fragments cloned were as follows: 436, 1.7 kb; 437, 2.0 kb; 438, 1.0 kb; 439, 0.7 kb; 441, 0.5 kb. The PVX fragments used to produce constructs 437, 438, 439 and 441 had the same 3' terminus, mapping to nucleotide postion 6391 in the PVX genome.

EXAMPLES

Example 1

The demonstration that an amplicon transgene activates gs involved a series of constructs in which potato virus X (PVX) cDNAs were introduced as transgene constructs into the tobacco genome.

Figure 1:
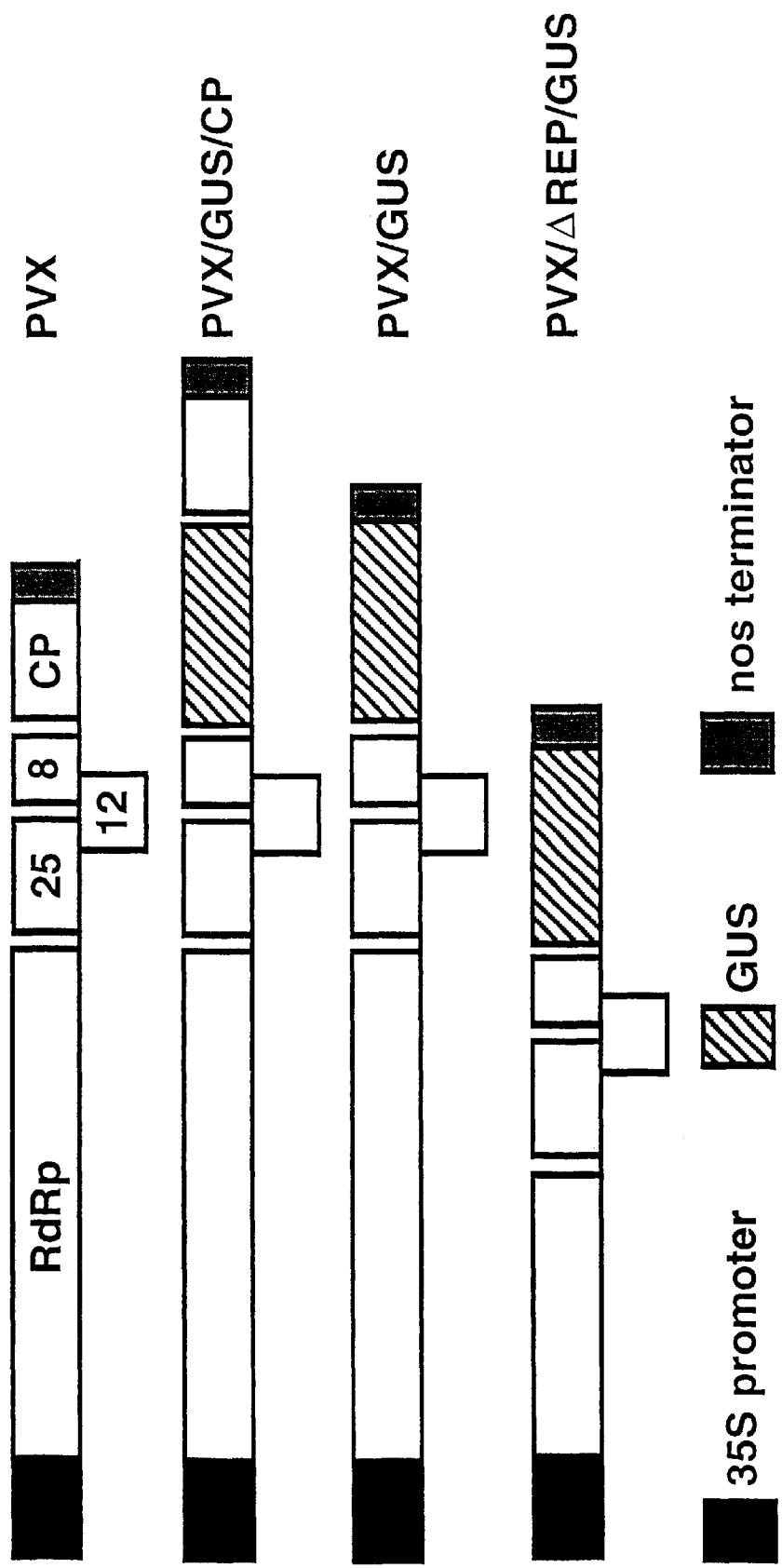
FIG. 1 illustrates 35S expressed amplicon constructs that were transferred to *N. tabacum* cv Petite havana plants by Agrobacterium mediated transformation. Each construct was inserted between the CaMV 35S promoter and the nos terminator sequence (Jones, J. D. G., et al (1992), *Transgenic Res.*, 1: 285–297). The various PVX ORFs are labelled: RdRp, RNA-dependent RNA polymerase; 25, 12, 8, the "triple gene block" genes (encoding proteins of 25, 12, and 8 kDa, respectively; CP, coat protein gene. The GUS sequence, shown as a hatched box, was inserted as an additional ORF in PVX/GUS/CP and was expressed from a duplicated CP subgenomic promoter, or as a direct replacement for the CP in PVX/GUS (referred to as pGC3S in Chapman, S. N., et al (1992), *Plant J.*, 2: 549–557). PVX/ΔREP/CP was essentially PVX/GUS but with a 1.7 kb deletion within the RdRp ORF to prevent the initiation of viral replication. Amplicon-mediated gs was observed in all plants expressing the PVX, PVX/GUS, or PVX/GUS/CP constructs.

FIG. 1 illustrates the PVX cDNA amplicon constructs that were assembled and introduced into Nicotiana tabacum cv Petite Havana by *Agrobacterium tumefaciens*-mediated transformation. One construct had the $PVX_{UK3}$ genome intact ("PVX"; FIG. 1). The other constructs were also based on the $PVX_{UK3}$ genome but were modified to include the β-glucuronidase (GUS) gene inserted either as an additional open reading frame (ORF) in the viral genome ("PVX/GUS/CP"; FIG. 1) or as a replacement for the coat protein ("PVX/GUS"; FIG. 1).

Both the PVX/GUS/CP and the PVX/GUS construct specified viral genomes that would not cause systemic infection if their RNA was inoculated to non transformed plants. In the PVX/GUS/CP construct there was a mutation in the PVX ORF 2 that encodes a protein required for movement of PVX out of the inoculated cell. The virus specified by the PVX/GUS construct would also remain confined to the inoculated cell because the infected cells would not produce coat protein.

A further amplicon construct pA209 that was tested in some of our experiments specified a defective PVX ORF3. As a result of this mutation the viral genome produced from the amplicon DNA, like that with the ORF2 and CP mutations, was movement defective. Plants were also transformed with a defective PVX/GUS construct encoding a non-functional RNA-dependent RNA polymerase ("PVX/ΔREP/GUS"; FIG. 1). The transgene-derived RNA from this construct would not initiate the viral replication cycle. Other control plants expressed GUS directly from the 35S promoter ("35S/GUS").

The amplicon lines selected for further detailed analysis were those in which there was a single transgene insert. These plant lines (5 to 7 independent lines for each construct) were identified by DNA gel blot analysis of the primary transformants ($T_0$ plants) and by the segregation ratios for GUS and/or the nptII gene in the T self progeny. ($T_1$ plants). However, the single locus nature of the inserts is not crucial: lines with multiple inserts behaved in the same way as those with single inserts.

It was concluded that the RNA transcribed from the amplicon constructs was replicated in the cells of the various transgenic lines because there was GUS activity in the lines carrying the PVX/GUS pA209 and PVX/GUS/CP constructs (Table I) and PVX particles in the lines in which the CP ORF was intact (PVX and PVX/GUS/CP). Production of GUS or CP was not due to direct translation of these proteins from the transgene-derived RNA because there was no GUS in the plants carrying the PVX/ΔREP/GUS construct.

The evidence that replication of the amplicon RNA in the transgenic plants had activated gs was from the analysis of amplicon-mediated gene expression and because there was resistance against PVX and suppression of transiently expressed DNA in the amplicon lines. The following paragraphs discuss these points in greater detail.

The first indication that expression of the wild type and derivative PVX RNAs ,was suppressed in the amplicon plants was the unexpected observation that these plants were completely free of viral symptoms. The initial indication that gs was active in the amplicon lines was from an analysis of the levels of GUS activity in the plants. The levels of GUS-activity in the amplicon plants were no higher and were as variable as, the levels in the 35S GUS lines. In the absence of gs it would be expected that the levels of GUS activity would be higher than in the 35S/GUS lines because of the amplification of the amplicon transcript by the replication process. The involvement of gs in the phenotype of the amplicon lines was also supported by histochemical staining which revealed that GUS activity was not detected in many of the cells of these plants. The absence of GUS was attributed to gs.

The GUS producing cells were evident as spots of histochemical staining in every plant expressing the PVX/GUS/CP or PVX/GUS transgene and in all organs of these plants including true leaves, stems, cotyledons, and roots. The spotted pattern of GUS activity was not observed in the plants expressing the 35S/GUS transgene. There are a number of possible explanations for the spotted appearance of the amplicon leaves after histochemical staining for GUS. In principle the spots could develop because the amplicon mediated gs is somatically unstable. However we consider that somatic instability is unlikely for several reasons: the regions of GUS production did not correspond to developmental sectors in the plant; the levels of amplicon RNA were not as high as would be expected if the gs was not active in all leaves of the plant and there was resistance against PVX even in regions of the amplicon leaves that stained blue for GUS. An alternative explanation is that the gs and associated homology dependent resistance is somatically stable in the amplicon plants but that the replicable amplicon RNA occasionally overcomes the effects of this gs. Resistance breaking, manifest as spots of GUS activity, would be more obvious in the GUS amplicon lines than in the PVX lines manually inoculated with PVX.GUS because the in planta transcription of the amplicon would generate a higher inoculation pressure than with a manually inoculated virus.)

The characteristic attributes of virus resistance by gs in transgenic plants are that it is specific to viruses that are very similar to the transgene at the nucleotide level and that it is often associated with low levels of the transgene RNA. Virus resistance with these characteristics is referred to as homology-dependent resistance.

To determine whether the amplicon lines (FIG. 1) exhibited homology-dependent resistance the amplicon plants of the $T_1$ generation were inoculated with $PVX_{UK3}$ which is the strain of PVX used as the original source of cDNA for the amplicon constructs.

Figure 2A:
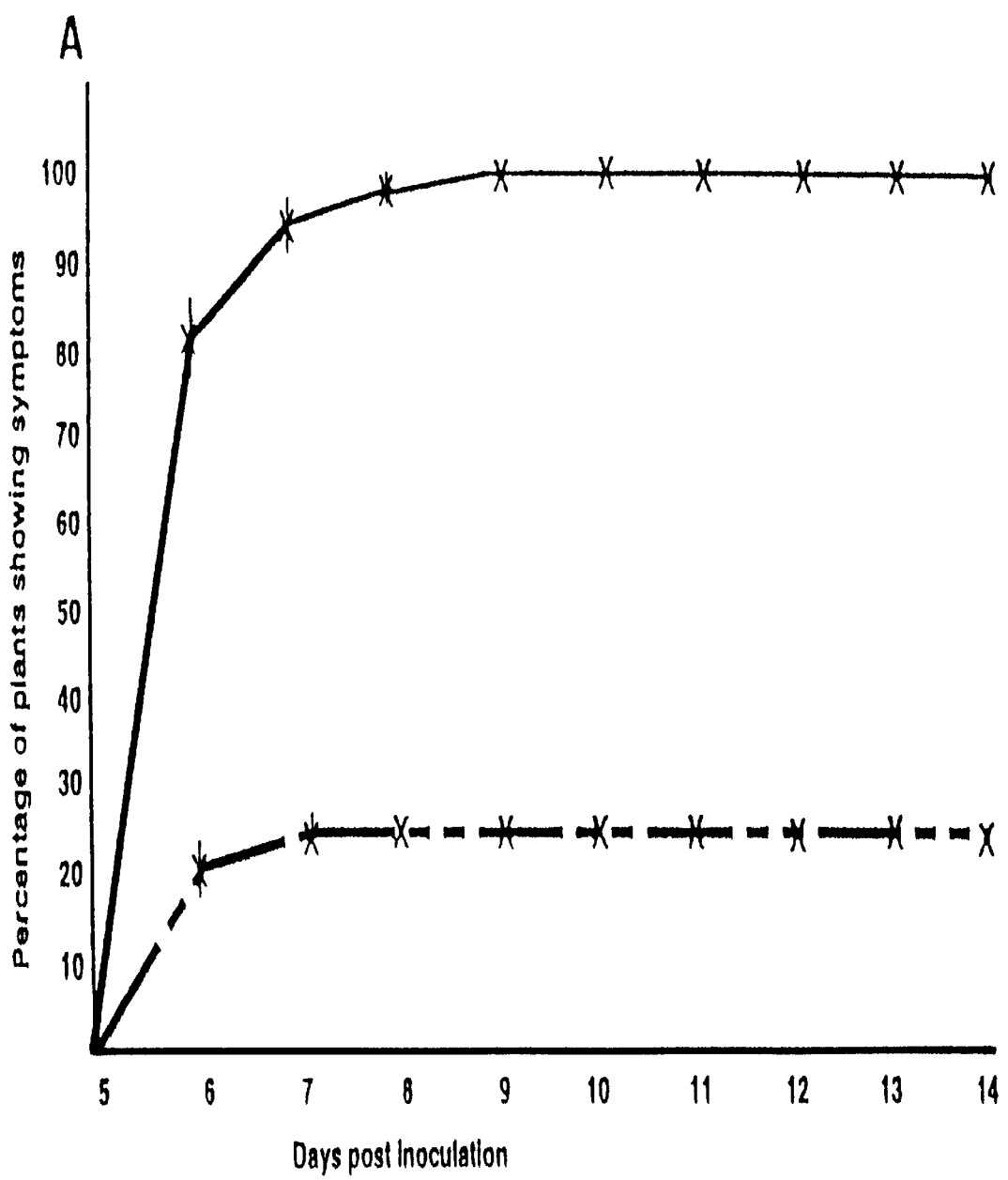
FIG. 2(a): Plants were inoculated with TXS (PVX strain UK3). Solid line, non-transformed plants and PVX/ΔREP/GUS plants (data pooled); dashed line, progeny of amplicon plants (PVX, PVX/GUS, and PVX/GUS/CP (data pooled)).
Figure 2B:
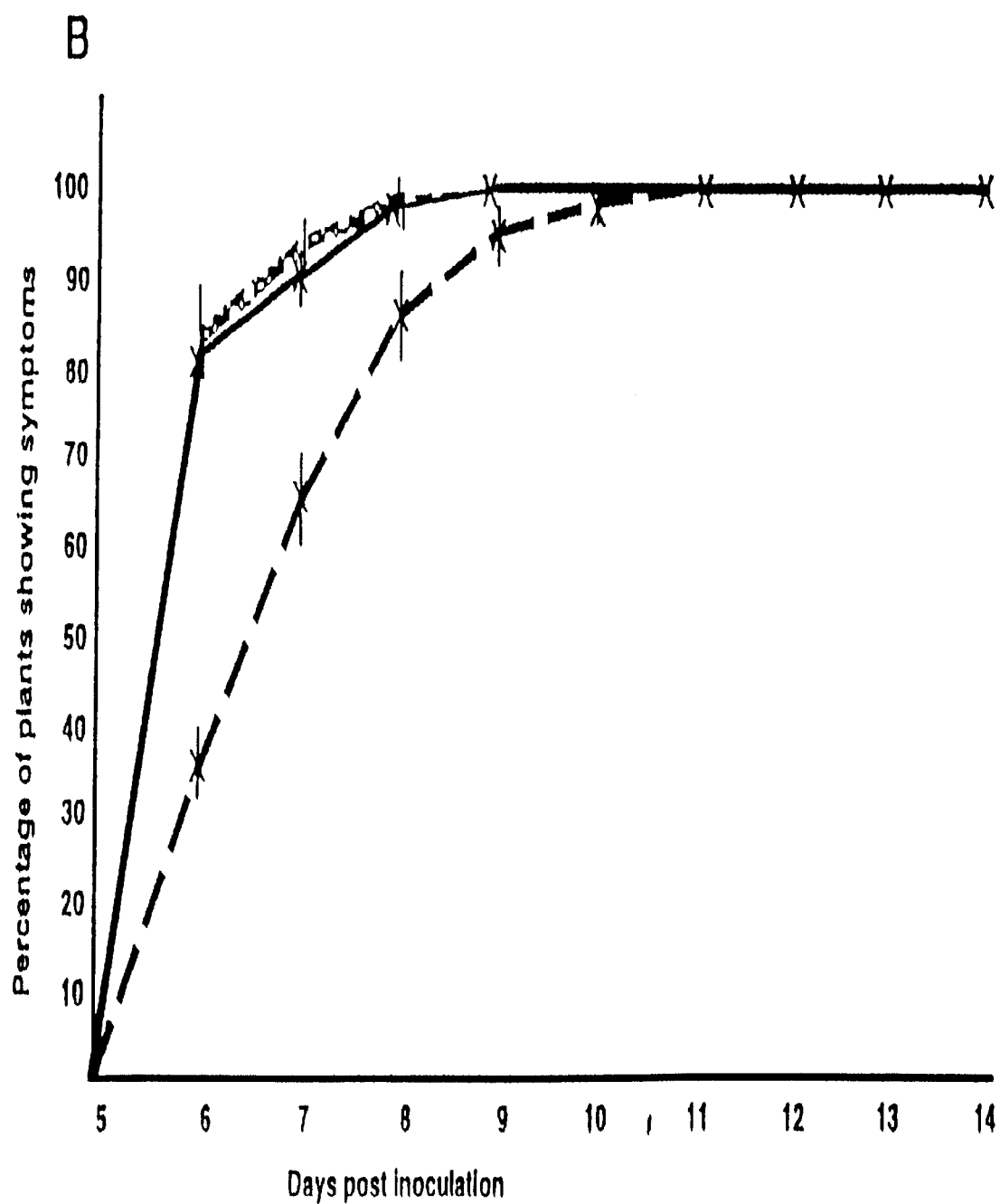
FIG. 2(b): Plants were inoculated with NL1, NL2, CP2 and CP4 strains of PVX (data pooled). Solid line, non-transformed and PVX/ΔREP/GUS plants; dashed line, amplicon plants expressing CP (PVX and PVX/GUS/CP (data pooled)); stippled line (which is partly obscured by the solid line), amplicon plants expressing PVX/GUS i.e. no CP present. Every plant showed symptoms of infection by 10 days post inoculation. A delay in the appearance of symptoms was observed with plants expressing a virus with CP.

Symptoms of PVX infection developed in 25% of the plants at the same time as in the plants expressing the PVX/ΔREP/GUS transgene or in the non-transformed plants. The remaining 75% of the amplicon plants failed to develop symptoms by 14 days post inoculation (all of the control plants showed symptoms within 9 days post inoculation) (FIG. 2).

This 3:1 segregation ratio of the resistance trait indicated that PVX resistance was expressed in most, if not all, of the transformed progeny of the amplicon lines. The data shown in FIG. 2 are combined from several independent experiments and are particularly notable for the lack of variation between plants and between lines generated with each construct.

In contrast, there was little or no resistance against the $PVX_{CP}$ and $PVX_{NL}$ strains. As the nucleotide sequence of $PVX_{CP}$ is 78% similar to the sequence of $PVX_{UK3}$ (30) it is concluded that the resistance in the amplicon lines is highly strain-specific.

To further analyse the strain-specific resistance a PVX.GFP construct was inoculated to non-transformed plants, to two PVX/GUS, two PVX/GUS/CP and two PVX/ΔREP/CP lines. PVX.GFP is a $PVX_{UK3}$ vector construct carrying the green fluorescent protein (GFP) reporter gene.

On the inoculated leaves of the non-transformed and PVX/ΔREP/GUS plants there were many large spots of green fluorescence at 7 days post inoculation illustrating infection of PVX.GFP on these plants. In contrast, there were no fluorescent regions on the leaves of the amplicon plants.

Similarly, PVX.GUS (the $PVX_{UK3}$ vector expressing the GUS reporter gene) produced large GUS-positive foci of infection on the PVX/ΔREP/GUS and non-transformed plants, but not on PVX plants. Infrequently, and after prolonged histochemical staining, there were 3 to 6 small spots of GUS activity visible on the leaves of PVX plants inoculated with PVX.GUS.

Based on these reporter gene data it was concluded that the absence of symptoms following inoculation of the amplicon plants with $PVX_{UK3}$ was due to resistance to initial infection rather than tolerance of PVX.

The conclusion that there was PVX resistance in the initially inoculated cell was confirmed by inoculation of PVX to protoplasts prepared from the transgenic plants. The inocula for these protoplast assays were in vitro synthesised transcripts of either pTXS or pCP2 which are full length cDNA clones of $PVX_{UK3}$ and $PVX_{CP2}$, respectively.

The protoplasts were prepared from plants expressing each of the amplicon constructs or from non-transformed control plants. The protoplasts were inoculated with in vitro synthesised transcripts of pTXS, the cDNA clone of $PVX_{UK3}$ (T) or pCP2, the cDNA clone of $PVX_{CP2}$ (C). RNA was extracted from 50,000 protoplasts 24 hours post inoculation and electrophoresed on a 1% (w/v) agarose-formaldehyde gel, blotted onto nylon membrane, and hybridised to an RNA probe specific for the 3' end of $PVX_{UK3}$ (T), or $PVX_{UK3}$ (C). Autoradiographs were exposed for 1 hour.

The RNA gel blot analysis of the protoplast extracts revealed that the genomic and subgenomic RNAs of both strains accumulated at high levels in the protoplasts of the non-transformed or the PVX/ΔREP/GUS lines. The $PVX_{CP2}$ RNA accumulated to the same extent in protoplasts of the amplicon and non-transformed lines. In contrast, the protoplasts of the amplicon lines displayed extreme resistance to $PVX_{UK3}$.

An important observation we made is that there is a low level of amplicon RNA in the mock inoculated cells of the PVX or the PVX/GUS/CP lines. In the cells of the PVX/GUS the amplicon transcripts were barely detectable even after long exposure of the autoradiograph. These observations confirm that the PVX resistance in the amplicon line was similar to homology-dependent resistance in that it was associated with low level accumulation of the transgene transcript.

Example 2

Virus resistance, as shown in Example 1 above, could be considered as trans-acting gs of viral genes. To demonstrate that the amplicons could also mediate trans-acting gs of nuclear genes a transient assay was performed.

Figure 3:
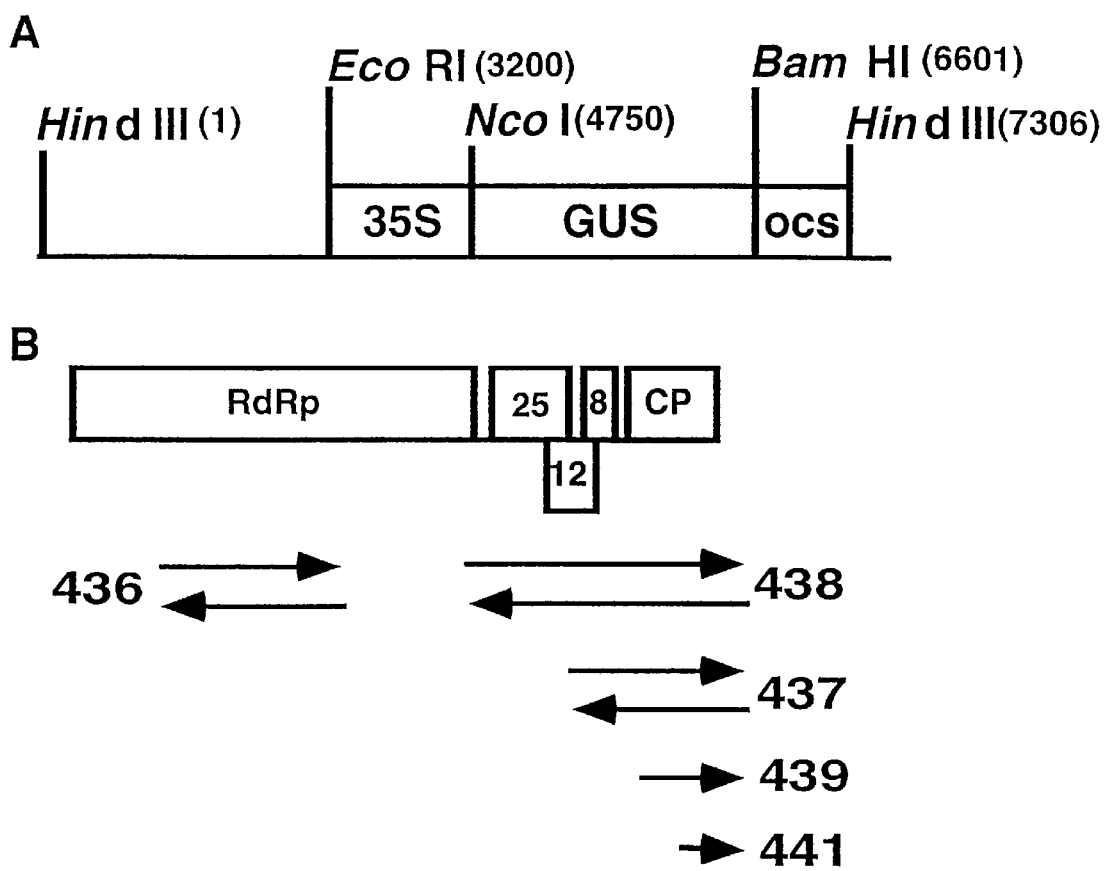
FIG. 3 shows the plasmid constructs used in the transient GUS expression assay (particle bombardment).

The constructs used in the transient assay were based on a plasmid expressing GUS directly from the 35S promoter (pSLJ4D4; FIG. 3). Regions of the $PVX_{UK3}$ cDNA clone were inserted on the 3' side of the GUS ORF. Sequences from either the 5' or 3' region of the viral genome were inserted into pSLJ4D4 in both sense and antisense orientations (FIG. 3). Each plasmid construct was coated onto gold particles and electrostatically bombarded into the leaves of plants expressing the PVX or PVX/ΔREP/GUS transgene or non-transformed plants.

Figure 4:
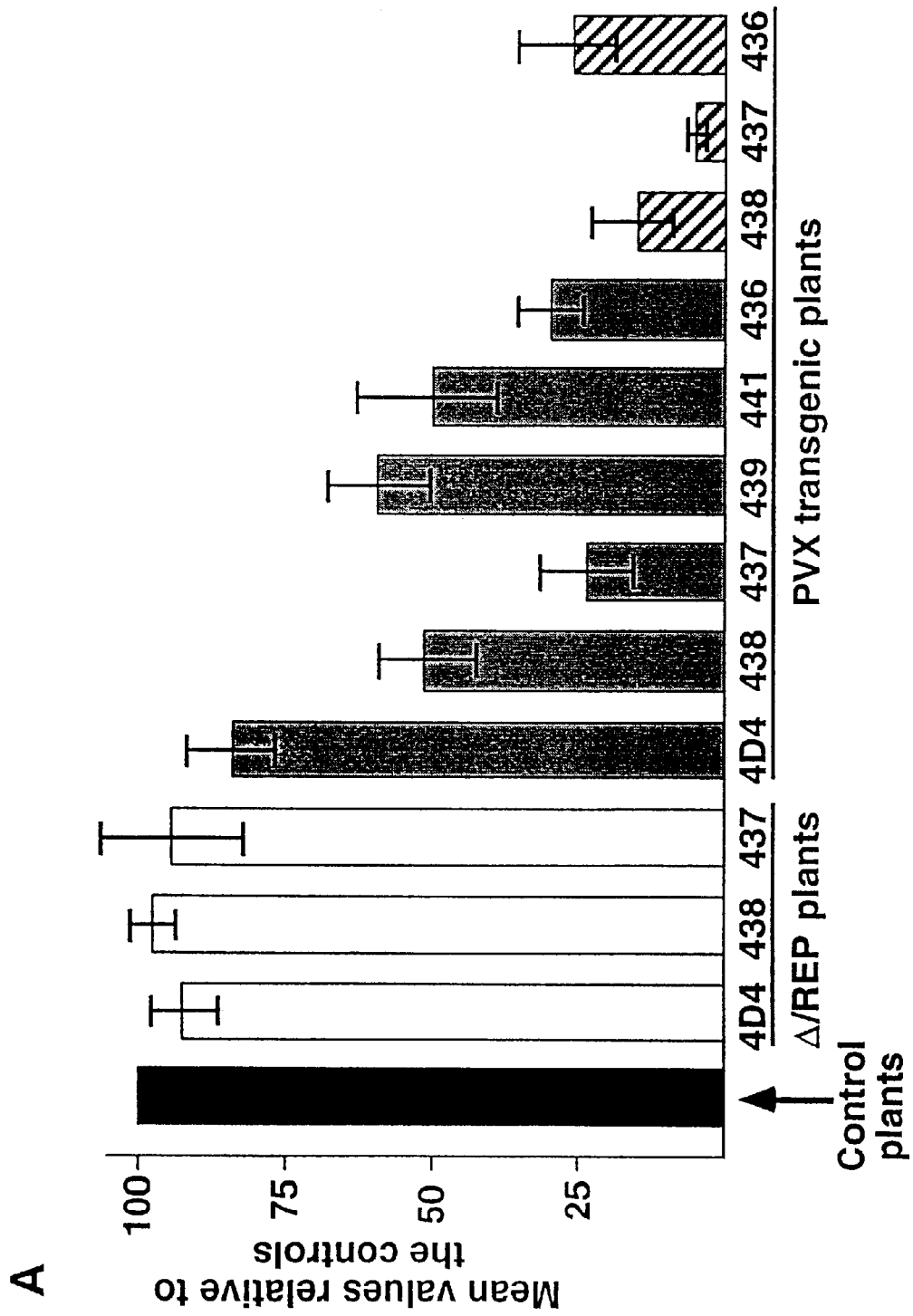
FIG. 4 shows the GUS activity in PVX and PVX/ΔREP/GUS amplicon leaf discs after particle bombardment with the constructs illustrated in FIG. 3. The leaf discs were stained for GUS activity 1 day post bombardment, cleared in 70% ethanol, and the number of blue spots were counted. The histograms are of mean numbers (+/−SE) of GUS positive spots on PVX/ΔREP/GUS (ΔREP) (white bars (sense constructs)) and PVX (light shaded bars (sense constructs) and hatched bars (antisense constructs)) leaf discs. Each experiment contained 6 to 8 control leaf discs excised from non-transformed plants (black bar). Experimental data were standardised such that the mean for the control discs in each experiment was 100. Each construct was bombarded into 9 PVX plants and 6 PVX/ΔREP/GUS plants (two leaf discs from each plant). For each construct the data have been pooled. T-tests showed that there was no significant difference in the number of spots with pSLJ4D4 on any plant (PVX, PVX/ΔREP/GUS or non-transformed), or with any construct on the non-transformed control plants compared with the PVX/ΔREP/GUS plants. The difference in the number of spots on the PVX plants with the GUS/PVX plasmids was significantly different (P>0.95) from the number on the non-transformed plants with these plasmids.

Histochemical staining for GUS activity of the bombarded leaves revealed that there was substantial and statistically significant suppression of GUS expression in the PVX plants, but only when the plasmid constructs contained a region of the PVX genome (FIG. 4). Suppression was manifested as a reduced number of blue spots on the PVX leaves compared with the number on the non-transformed control plants (FIG. 4). Based on the number of blue spots in this transient assay, the GUS expression in the PVX plants was 50 to 90% less than that observed in the non-transformed plants.

Expression of GUS from the plasmids with the PVX sequences transcribed in the antisense orientation was suppressed at least as well as from those where the PVX sequence was transcribed as sense RNA.

No suppression of GUS expression in the transient assay was ever observed in the plants with the PVX/ΔREP/GUS transgene (FIG. 4).

There was no suppression of GUS expression from pSLJ4D4 which has promoter homology with the amplicon transgene (FIG. 4). It is likely therefore that the suppression of GUS expression from the GUS/PVX chimeric constructs involved a post-transcriptional mechanism in the amplicon plants. This mechanism resembles post-transcriptional gs in that it targets viral RNAs and RNAs transcribed from transiently expressed nuclear genes. Presumably the PVX sequence at the 3' end of the GUS/PVX transcript from the transiently expressed plasmid was the target of a mechanism of post-transcriptional gs on the amplicon plants expressing the PVX transgene.

Example 3

It was not possible to use the biolistic transient assay of gene silencing in the lines with PVX/GUS and PVX/GUS/

CP amplicons because the bombardment procedure led to high background levels of GUS. In order to analyse gene silencing in these lines an alternative transient assay of gs was performed.

The 35S/GUS sequence from pSLJ4D4 was transferred to a binary vector. *Agrobacterium tumefaciens* cultures carrying this construct were infiltrated into leaves of the amplicon plants and GUS expression ascertained by histochemistry staining. Expression of GUS was suppressed in both the PVX/GUS and the PVX/GUS/CP plants but not the PVX plants. Preliminary data suggest that the PVX/GUS amplicon is a better silencer of GUS than the PVX/GUS/CP construct.

In similar experiments the 35S/GUS/PVX sequence from plasmid 437 was transferred to a binary vector and introduced into the amplicon plants via Agrobacterium infiltration. Histochemical analysis revealed that GUS expression from the 437 construct was suppressed in PVX plants PVX/GUS plants.

The reproducibility of the amplicon gs is indicated by the above tests in which all amplicon lines tested exhibited a similar phenotype. A Table is presented (Table I) to show the number of lines used for each test.

TABLE I

| ANALYSIS | NO. OF LINES TESTED |
| --- | --- |
| Virus resistance | 24 |
| Bombardment | 5 |
| Agrobacterium Infiltration | 8 |

Example 4

Figure 5:
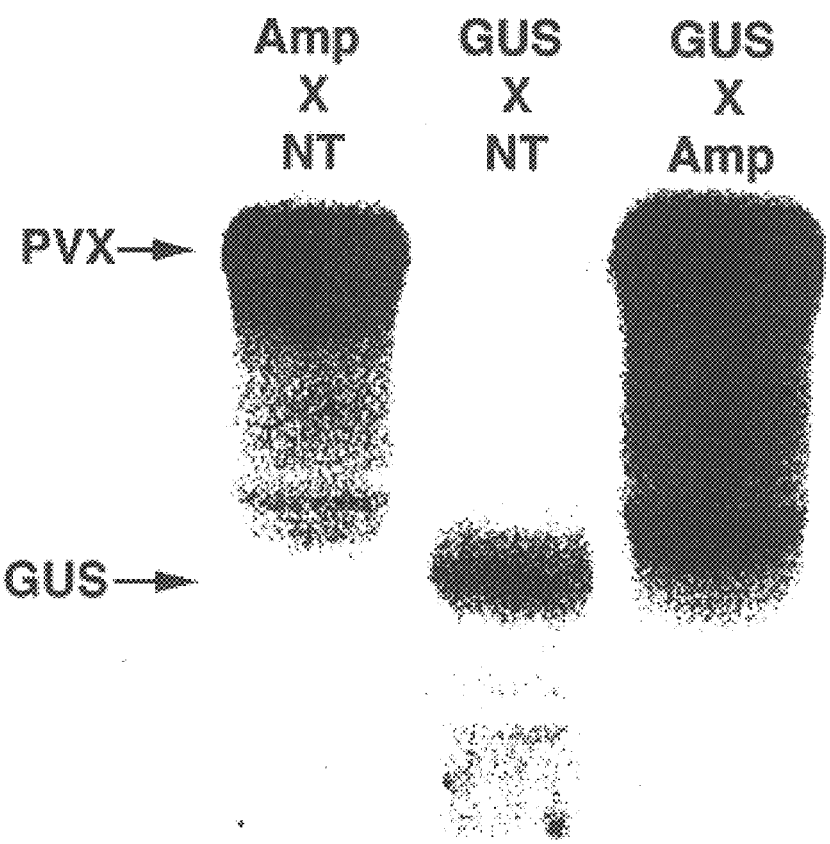
FIG. 5 shows a gel blot analysis of RNA extracted from amplicon X 35S/GUS plants. RNA was extracted from plants expressing a PVX/GUS/CP amplicon (Amp X NT), or expressing a 35S/GUS transgene (GUS X NT), or expressing both the PVX/GUS/CP amplicon and 35S/GUS transgene (GUS X Amp). The presence of the transgenes was confirmed by PCR analyses and Southern hybridisations. 5 micrograms of total RNA was electrophoresed on a 1% gel. The entire GUS sequence was used as a probe. The arrows indicate the GUS mRNA (GUS) and amplicon RNA (PVX) that was encapsidated.

In a third assay of amplicon gs the amplicon lines (PVX/GUS, PVX/GUS/CP & PVX/ΔREP/GUS) were crossed to lines carrying a 35S/GUS transgene. RNA gel blot analysis showed a suppression of GUS mRNA in plants carrying both the amplicon and 35S/GUS trangenes compared to plants carrying the 35S/GUS transgene alone (FIG. 5).

These data indicate that the amplicon can mediate gs of a nuclear gene with homology to the amplicon construct.

Reciprocal crosses were made between the *Nicotiana tabacum* cv. Petite amplicon plants (PVX or PVX/GUS or PVX/ΔREP/GUS) or non-transformed control plants) and 35S/TGB12+8 transgenic plants. The 35S/TGB12+8 plants express the PVX 12 kDa and 8 kDa triple gene block proteins. These plants show an extreme dwarf phenotype and have chlorotic and necrotic leaves.

Figure 6:
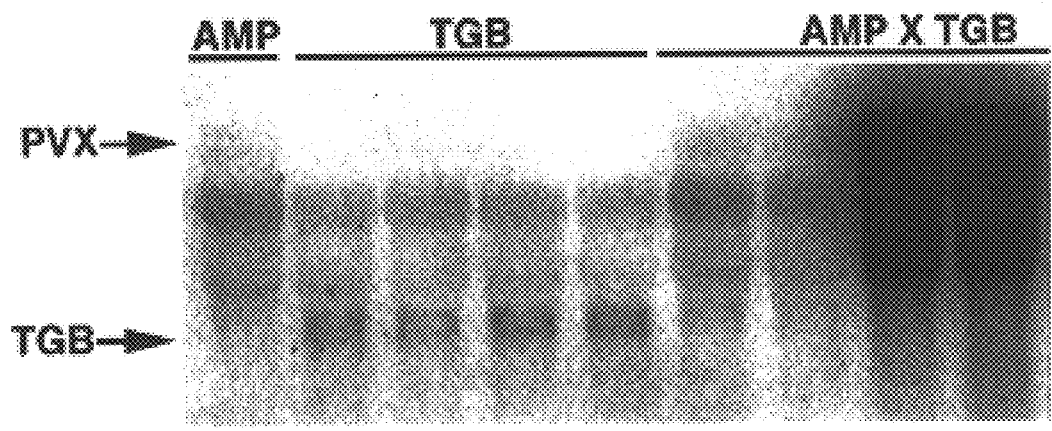
FIG. 6 shows a gel blot analysis of RNA extracted from the amplicon X TGB plants. RNA was extracted from the plants expressing an amplicon, an amplicon plus 35S/TGB transgene, or the TGB transgene alone. Track 1 shows RNA extracted from a PVX/GUS plant (AMP). Tracks 2 to 5 show RNA extracted from 35S/TGB12+8 transgenic plants (TGB). Tracks 6 and 7 show RNA extracted from plants expressing a PVX/GUS amplicon and the 35S/TGB12+8 transgene (AMP X TGB). Tracks 8 and 9 show RNA extracted from plants expressing both the 35S/TGB12+8 transgene and a PVX amplicon (AMP X TGB). The probe used was the entire TGB 12+8 coding sequence. The arrows indicate the encapsidated viral RNA (PVX) or the TGB mRNA (TGB).

All plants expressing both the PVX amplicon and the 35S/TGB12+8 transgene were wild-type in appearance, that is they lost the chlorosis and necrosis and were of normal size. All plants expressing both the PVX/ΔREP/GUS amplicon and the 35S/TGB12+8 transgene showed the TGB phenotype, consistent with the hypothesis that replication of the amplicon is required to trigger the gene silencing mechanism. RNA gel blot analysis confirmed that the TGB mRNA was reduced in the plants silenced by the amplicon (FIG. 6).

Example 5

Figure 7:
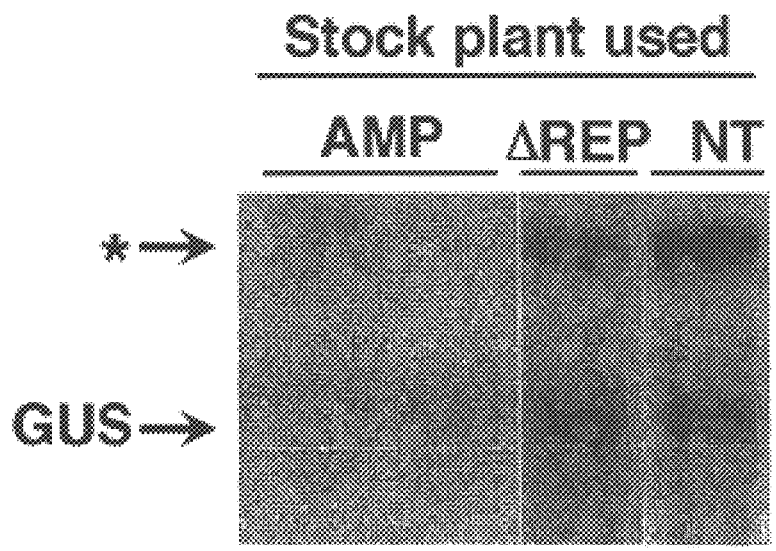
FIG. 7 shows a gel blot analysis of RNA extracted from 35S/GUS scions. RNA was extracted 5 weeks post grafting from the 35S/GUS scions. The stock plants were a PVX/GUS amplicon (AMP) or a PVX/DREP/GUS amplicon (DREP) or non-transformed control plants (NT). 5 micrograms of total RNA was electrophoresed on a 1% gel. The entire GUS sequence was used as a probe. The GUS arrow indicates the GUS mRNA. The asterix points to a second larger GUS transcript that is produced in the 35S/GUS line (SA94084). A similar reduction in GUS mRNA was observed in two other 35S/GUS lines tested, that do not produce this second GUS transcript, when they were inoculated to GUS amplicon plants.

In a fourth assay of amplicon gs, the 35S/GUS transgenic plants were grafted onto amplicon plants (PVX/GUS/CP, PVX/GUS, PVX, or PVX/ΔREP/GUS) or non-transformed (NT) control plants. Gel blot analysis on RNA extracted from the 35S/GUS scions showed that the GUS mRNA was reduced when the stock plant expressed a replicating PVX/GUS or PVX/GUS/CP amplicon (FIG. 7). These data indicate that the amplicon produces a systemic signal of gs which can suppress expression of a transgene with homology to the amplicon construct.

This indicates that the systemic or remote amplicon induced gs may be observed in those embodiments wherein not all cells in a plant are transcribing the amplicon encoding nucleic acid, for instance because it has not been introduced throughout the plant, or because transcription is under the control of an inducible or tissue- or developmentally-regulated promoters.

Example 6

In a futher assay of amplicon gs, part of the tomato dwarf gene was inserted into a PVX/GUS amplicon. The resulting contruct, PVX/GUS/DWARF, was introduced into tomato plants using *A. tumefaciens*-mediated transformation. Histochemical staining revealed spots of GUS activity on the transformed plants, similar to the pattern of GUS staining observed on tobacco plants expressing a PVX/GUS or PVX/GUS/CP amplicon. This observation suggested that the PVX/GUS/DWARF amplicon was expressed and viral replication had induced gs in the tomato plants. All of the plants expressing the PVX/GUS/DWARF amplicon showed reduced plant height compared to non-transformed control plants taken through the tissue culture procedure at the same time (plants were assessed 3–4 weeks after being transferred to rooting media, and were grown at 24° C. with 16 hours of illumination. These data indicate that the amplicon can activate reproducible gs in tomato and can suppress expression of an endogenous gene.

Example 7

Amplicon gs does not rely on use of the 35S promoter of CaMV. We have repeated the transformations described above with constructs that are similar to the 35S promoter constructs shown in FIG. 1 except that they have the nos promoter of *Agrobacterium tumefaciens*.

Analyses performed on the primary transformants revealed that the plants showed little or no GUS activity (nos/PVX/GUS and nos/PVX/GUS/CP plants), but contained virions (nos/PVX and nos PVX/GUS/CP plants), similar to the observations made with the 35S expressed amplicons.

The nos amplicon plants were infiltrated with Agrobacterium cultures carrying a 35S/GUS plasmid and infiltrated leaves stained for GUS activity 2 days post infiltration. Panels of GUS activity were observed on leaves from non-transformed control plants and from leaves expressing a nos/PVX or nos/PVX/ΔREP/GUS amplicon. GUS activity from the transiently expressed plasmid was not observed in leaves expressing a nos/PVX/GUS or nos/PVX/GUS/CP amplicon.

These data indicate that the nos amplicons act in the same way as the 35S amplicons in that they can mediate reproducible gs.

Example 8

PVX amplicons may be used in a range of plants including those that are not natural hosts of PVX.

To demonstrate this host range aspect of the amplicon phenotype, a series of amplicon constructs were assembled that are similar to those shown in FIG. 1 with the exception that the GUS sequence was replaced with cDNA encoding the jellyfish green fluorescent protein (GFP). These GFP amplicon constructs were essentially identical to the PVX.GFP vector constructs that have been described previously (in Baulcombe et al. (1995), *Plant7*: 1045–1053). These constructs were transformed into *Arabidopsis thaliana* which is not a host for PVX.

The transgenic plants contained particles (virions) of PVX.GFP indicating that the RNA transcript of the amplicon had undergone replication in Arabidopsis. Seedlings transformed with a PVX/GFP/CP amplicon showed green fluorescence from the GFP reported gene at the tips of the very first true leaves only. GFP was not detected in older plants.

Additionally, a plant was inoculated with sap extracted from an Arabidopsis plant transformed with a PVX/GFP/CP amplicon. A leaf was illuminated under UV light and showed spots of GFP activity indicating the presence of PVX/GFP/CP virions in the Arabidopsis sap extract.

The Progeny of these transformed Arabidopsis also contained particles of PVX.GFP indicating that the amplicon was integrated into the nuclear genome and inherited. However, despite the presence of PVX.GFP particles there was no detectable GFP in these lines.

Thus, the phenotype of these Arabidopsis lines parallels the phenotype of the transgenic tobacco plants described above: there is virus replication but there is suppression of the reporter gene (GFP in this case) that is part of the amplicon construct. These features are strong indicators that there is gs due to the presence of the amplicon in the genome of Arabidopsis.

In a further experiment, Arabidopsis plants were transformed with a 35S/GFP transgene. These plants were cross pollinated with plants expressing a PVX/GFP/CP amplicon or with non-tranformed (NT) control plants. Both the parental 35S/GFP transgenic plants and the progeny from the cross 35S/GFP X NT showed uniform GFP expression. However, every plant expressing both the PVX/GFP/CP amplicon and the 35S/GFP transgene showed no GFP activity. The 35S/GFP transgenic plants were also transformed again with a PVX/GFP amplicon. The resulting transgenic plants showed no GFP activity despite carrying the 35S/GFP transgene. These observations indicate that the amplicon can mediate reproducible gs in Arabidopsis.

Example 9

Figure 8:
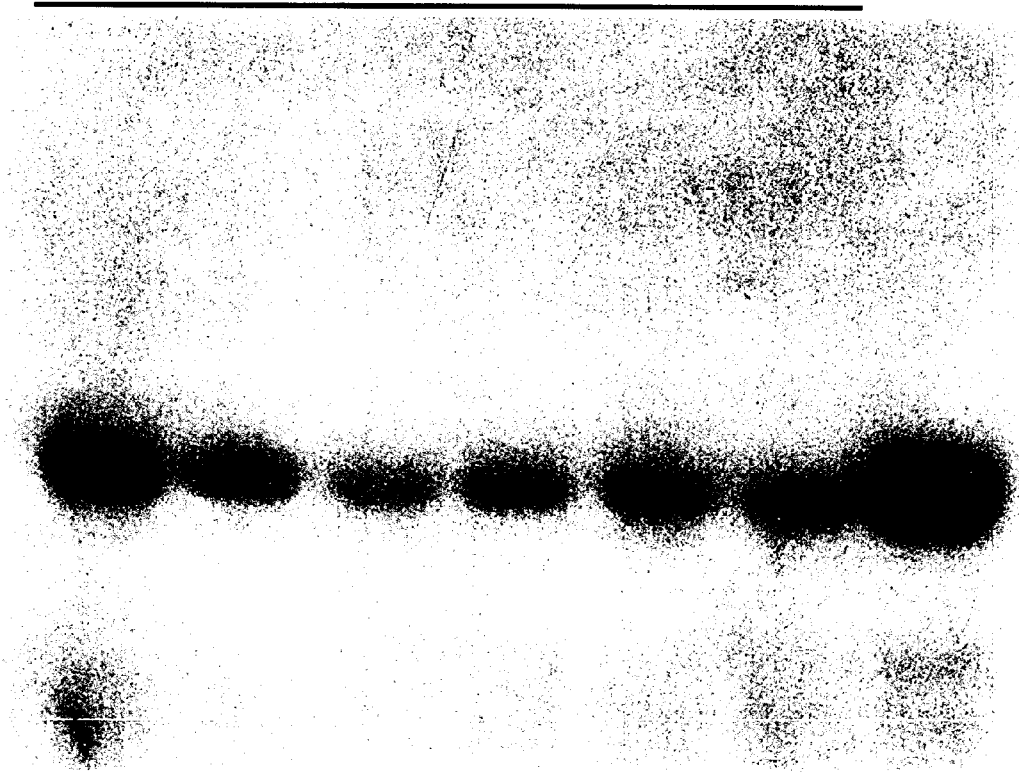
FIG. 8 shows a gel blot analysis of RNA extracted from Arabidopsis plants expressing a PVX/GUS/AtrbohD amplicon (Amplicon plants) or non-transformed control plants (C). The probe used was the 5' end of AtrbohD.

To demonstrate that amplicons can mediate reproducible gs of endogenes in Arabidopsis, part of the phytoene desaturase (PDS), ALBINO3, and *A. thaliana* respiratory burst oxidase homologue D (AtrbohD) endogenes were separately cloned into a PVX amplicon and were transformed into Arabidopsis. Every transformant expressing a PVX/PDS or PVX/ALBINO amplicon showed white spots on the leaves, and AtrbhoD mRNA levels were suppressed in every transformant expressing the PVX/AtrbhoD amplicon (FIG. 8). These data demonstrate that the amplicon can mediate reproducible gs of endogenes in plants, even those which are not natural hosts for PVX. Thus amplicon-mediated gs may be used with endogenous genes including those responsible or associated with traits such as ripening, pollen formation, lignin biosynthesis, flower pigment production, regulatory pathways controlling development, environmental responses (e.g. growth habit or disease resistance), toxin production etc.

Conclusions From Example Above

The experimental evidence described above provides indications that amplicon constructs can cause gs of multiple targets. In the 35S/PVX/GUS lines there is homology-dependent resistance against both PVX and suppression of GUS in the transient assay.

Amplicon constructs may be useful activators of gs, even with further elements deleted from the constructs shown in FIG. 1. Thus constructs based on those disclosed above, but comprising only a minimal amplicon, wherein all sequence from the viral construct that does not encode proteins required for replication or that does not include cis-acting elements required for replication, has been eliminated. It should also be noted that gs apparently does not require the target sequence to be attached to a viral promoter because the 5' region of the viral genome which is not in a viral subgenomic RNA is a target of gene silencing.

Example 10

Comparison With the Approach Suggested by Biosource Technologies in WO95/34668

The work of Biosource Technologies Inc (20,21) can be considered as following from the potyviral transgenes work (22) mentioned above, although the sequence similarity between the virus and the nuclear genome involves an endogenous nuclear gene rather than a transgene and there is no characterization of the virus induced gs on virus accumulation.

The paper (21—Kumagai et al.) and the associated patent application (20) describe two types of examples involving TMV vectors.

In one of these the cDNA sequence inserted into the vector was of phytoene desaturase mRNA and there is virus-induced silencing of the endogenous phytoene desaturase gene. A second example involves phytoene synthase cDNA added into the TMV vectors. In this example there is no silencing of the endogenous gene. In fact there was over-expression of the phytoene synthase. The differences between these two examples are further evidence that virus induced gene silencing is not necessarily a reproducible phenomenon.

An additional important point about variation in virus-induced gene silencing has been demonstrated by our further experimental analysis of the Biosource documents.

These analyses have revealed that virus induced gene silencing varies between plant species. We have produced a virus vector construct similar to their TMV/phytoene desaturase construct. The only major difference between our construct and the specific Biosource experiments is that the virus vector is potato virus X rather than TMV. However, this difference is not likely to influence the outcome of the experiments because a PVX construct, like the TMV construct is able to initiate silencing of the endogenous PDS gene when inoculated to Nicotiana benthamiana. This vector is also able to silence the PDS of Nicotiana clevelandii.

However, there is no silencing of the PDS gene of Lycopersicon esculentum even though this plant is a recognised host of PVX.

We introduced a fragment of the tomato phytoene desaturase (PDS) cDNA into the PVX vector and inoculated to Nicotiana benthamiana, Nicotiana clevelandii and Lycopersicon esculentum (tomato). The fragment of tomato PDS sequence inserted into the PVX vector was exactly the same as the fragment added to the TMV vector in the experiments of Kumagai et al. (21). When the PVX/PDS vector constructs were inoculated to the Nicotiana species, as described by Kumagai et al with the TMV constructs, there was photobleaching of the upper parts of the plant indicating that there had been gs of the endogenous PDS genes. However, when the same PVX/PDS constructs were inoculated to tomato, despite tomato being a good host of PVX and despite the identity of the viral PDS sequence and the endogenous sequence there was no photobleaching and therefore no gs of the tomato PDS.

The failure to get photobleaching could not be attributed to lack of infection: there were PVX symptoms on the infected plants and PVX/PDS RNA had accumulated to a high level.

In a similar experiment the cDNA (between the starcodon at position 105 to the stop codon of the open reading frame at position 1542) of glutamate semialdehyde aminotransferase (GSA-AT2) of *Nicotiana tabacum* was inserted into the PVX vector (Hofgen et al., (1994) *Proc. Natl. Acad. Sci. USA* 91: 1726–1730). In this experiment there was strong gs of the endogenous GSA-AT2 sequence after inoculation to *N. benthamiana* and the infected plants developed a yellow chlorosis. However after inoculation to *N. tabacum* there was much weaker gs and only a very mild chlorosis.

These results illustrate differences between the amplicon gs and the virus-induced gs of the Biosource documents. Amplicon gs does not rely on the ability of the virus to move in the infected plant and may be used even with plants that are not recognised hosts of the virus used as a component of the amplicon construct. Amplicon gs is useful even when the amplicon specifies a defective construct that does not move from cell to cell in the infected plant. In plant species in which the amplicon transcripts replicate, our experiments show the gs is consistent from plant to plant.

On the other hand, our experiments show that gs induced by an inoculated virus is subject to plant to plant variation associated with environmental effects on virus spread. It is an effect that does not operate equally well even in different hosts of the virus vector and our experiments show it does not have the consistency achieved using the present invention.

This influence of the host plant does not apply to amplicon-mediated gene silencing in accordance with the present invention, which, as indicated above, is effective in plants that may or may not be a natural host for the viral component of the amplicon construct.

Materials and Methods

Constructs and Plant Transformation

All of the viral cDNA constructs were inserted between the CaMV 35S promoter and the transcriptional terminator of the nopaline synthase (nos) gene and transferred into the binary vector pSLJ7291. Details of each construct are given below.

An infectious PVX cDNA clone was inserted between the CaMV 35S promoter and the transcriptional terminator of the nopaline synthase (nos) gene to generate the plasmid, pNCX. The 7.3 kb NarI fragment encompassing the 35S promoter, the entire PVX genome, and terminator sequence was ligated with ClaI digested binary vector, PSLJ7291, to create the PVX transgene construct (FIG. 1).

The 1.4 kb ApaI-XhoI fragment from pNCX was replaced with the corresponding fragment from plasmid ΔG (7) to generate plasmid pA100. Plasmid pA100 is a pUC-based vector encoding the 35S promoter, PVX orfs 1,2,3,4, GUS and terminator sequence. A CP subgenomic promoter sequence upstream of the GUS gene allowed GUS to be expressed as part of a subgenomic RNA (7). The 8.6 kb NarI fragment from pA100 was ligated with ClaI digested pSLJ7291, to create the PVX/GUS transgene construct (FIG. 1).

A 1.7 kb BglII fragment was deleted from PVX orf1 in plasmid pA100 to generate pA102. The 6.9kb NarI fragment from pA102 was ligated with ClaI digested pSLJ7291 to create the PVX/ΔREP/GUS transgene construct (FIG. 1).

The 1.4 kb ApaI-XhoI fragment from pNCX was replaced with the corresponding fragment from plasmid pΔApa/Apa-GUS (which is construct GC3 (7) containing a 324nt deletion in orf2) to generate plasmid pA104. Plasmid pA104 is a pUC-based vector encoding the 35S promoter, PVX orf1, a mutated orf2, orfs 3 and 4, GUS, CP and terminator sequence. A duplicated CP subgenomic promoter sequence upstream of the GUS gene allowed GUS to be expressed as part of a subgenomic RNA (7). The deletion in PVX orf2 disrupts cell-to-cell movement, but has little or no effect on viral accumulation in protoplasts (2). The 9.0 kb NarI fragment from pA104 was ligated with ClaI digested pSLJ7291, to create the PVX/GUS/CP transgene construct (FIG. 1).

The 35S/GUS construct (FIG. 1) was generated by digestion of pSLJ4D4.(FIG. 3) with EcoRII and HindIII and the 4.1 kb fragment encoding the 35S promoter, GUS and terminator sequence was ligated with the similarly digested binary vector, pSLJ7292, to generate the 35S/GUS transgene construct (FIG. 1). Plasmid pSLJ7292 is identical to pSLJ7291 except for the orientation of the polylinker sequence.

Each construct was introduced into *N. tabacum* cv Petite havana by *A. tumefaciens* mediated leaf disc transformation (15) and plants were regenerated on medium containg kanamycin (30 μg/ml).

For the DWARF constrcut, 1 kb of the 5' end of the tomato DWARF gene was inserted into the XhoI site of the 35S/PVX/GUS amplicon. The 9.6 kb 35S/PVX/GUS/DWARF SstI fragment was ligated with SstI cut pSLJ7291. The construct was introduced into tomato cv Money Maker by *A. tumefaciens* mediated leaf disc transformation (15) and plants were regenerated on medium containing kanamycin (300 micrograms/ml).

Other constructs (PVX/AtrbohD, PVX/ALBINO3, and PVX/PDS1) were constructed by introducing approximately 0.5–1.0 kb of each target gene into the XhoI site of the 35S/PVX/GUS amplicon construct. Each construct was transferred into the binary vector pGREEN0029 (PVX/PDS and PVX/ALBINIO3) or pSLJ755 (PVX/AtrbohD) and introduced into *A. thaliana* plants by flower transformation. Transgenic seedlings were selected after treatment with basta.

Analysis of GUS Activity

Histochemical staining for GUS activity was performed on $T_0$ and $T_1$ plants, as described (1). MUG assays on $T_1$ plants (5 weeks old) were performed as described (7). For each plant, leaf discs were excised from three different leaves and the sap extract pooled. Preparation of PVX Virions and Virion RNA The preparation of virions and virion RNA was as described previously (6).

Transcription in Vitro, Preparation and Electroporation of Protoplasts, and RNA Gel Blot Analyses The plasmids pTXS and pCP2 were linearised with SpeI restriction enzyme and transcribed in vitro as described (7). The preparation and inoculation of protoplasts and RNA gel blot analysis were as described (7).

Plasmid Constructs for Leaf Disc Bombardment

Fragments of the PVX genome (FIG. 3) were generated by the polymerase chain reaction using oligonucleotide primers that contained a BamHI restriction enzyme site in addition to the PVX sequence. The template DNA was pTXS (the full-length cDNA clone of PVX$_{UK3}$). The reactions were performed as described previously (7).

The DNA products were digested with BamHI and ligated with BamHI digested pSLJ4D4 to generate the plasmids 437, 438, 439, and 441. The 1.7 kb BglII fragment from pTXS was ligated with BamHI digested pSLJ4D4 to generate the plasmid 436. The orientation of the PVX sequence in pSLJ4D4 was determined by restriction enzyme analyses. The PVX fragments used for constructs 436, 437 and 438 were individually cloned in both sense and antisense orientations (FIG. 3).

Leaf Disc Bombardment

Leaf discs were excised from fully expanded leaves from 6 week old plants and placed onto Murashige and Skoog medium containing 3% sucrose and were immediately bombarded with gold particles coated with plasmid DNAs. Plasmid DNAs were prepared using a QIAGEN-tip 100 column (Qiagen Inc. Dorking, Surrey) and were precipitated onto 0.95 μm diameter gold particles as described (25), but with a further 20-fold dilution of the preparation. Particle acceleration was performed using the ACCELL gene delivery system (Agracetus Inc.) under partial vacuum using a helium pressure of 10,000 kPa. The leaf discs were incubated at RT in the dark for 24 h and then stained for GUS activity.

REFERENCES

1. Angell, S. M. and Baulcombe, D. C. (1995) *Plant J.*, 7, 135–140.
2. Angell, et al. (1996) *Virology*, 215, 197–201.
3. Baulcombe, D. C. (1996) *Plant Molecular Biology*, 32, 79–88.
4. Baulcombe, D. C. and English, J. J. (1996) *Current Opinion In Biotechnology*, 7, 173–180.
5. Baulcombe et al. Gene silencing and virus resistance in transgenic plants. In: *Mechanisms and applications of gene silencing*, edited by Grierson, D., Lycett, G. W. and Tucker, G. A. Nottingham: Nottingham University Press, 1996, p. 127–138.
6. Baulcombe et al. (1984) *Plant Pathol.*, 33, 361–370.
7. Chapman et al. (1992) *Plant J.*, 2, 549–557.
8. Davies et al. (1993) *Virology*, 197, 166–175.
9. Donson et al. (1994) U.S. Pat. No. 5,316,931.
10. English et al. (1996) *Plant Cell*, 8, 179–188.
11. Finnegan, J. and McElroy, D. (1994) *Bio/Technology*, 12, 883–888.
12. Flavell, R. B. (1994) *Proc. Natl. Acad. Sci. USA*, 91, 34907–3496.
13. Hobbs et al. (1990) *Plant Mol. Biol.*, 15, 851–864.
14. Hobbs et al. (1993) *Plant Mol. Biol.*, 21, 17–26.
15. Horsch et al. (1985) *Science*, 227, 1229–1231.
16. Jorgensen, R. A. (1992) *AgBiotech News and Information*, 4, 265–273.
17. Jorgensen, R. A. (1995) *Science*, 268, 686–691.
18. Kaido et al. (1995) *J. Gen. Virol.*, 76, 2827–2833.
19. Kooter et al. (1994) *Journal Of Cellular Biochemistry*, 115.
20. Kumagai et al. (1995) WO95/34668.
21. Kumagai et al. (1995) *Proc. Natl. Acad. Sci. USA*, 92, 1679–1683.
22. Lindbo et al. (1993) *Plant Cell*, 5, 1749–1759.
23. Matzke, M. A. and Matzke, A. J. M. (1995) *Trends In Genetics*, 11, 1–3.
24. Matzke, M. A. and Matzke, A. J. M. (1995) *Plant Physiol.*, 107, 6679–685.
25. McCabe et al. (1988) *Bio/Technology*, 6, 923–926.
26. (deleted)
27. Mori et al. (1996) *Febs Lett.*, 1, 171–174.
28. Mueller et al. (1995) *Plant J.*, 7, 1001–1013.
29. Napoli et al. (1990) *Plant Cell*, 2, 279–289.
30. Santa Cruz, S. and Baulcombe, D. C. (1995) *J. Gen. Virol.*, 76, 2057–2061.
31. Suzuki et al. (1996) *Febs Lett.*, 379, 26–30.
32. Turpen, T. H. (1994) WO94/16089.
33. Turpen et al. (1996) WO96/12028.
34. Van Blokland et al. (1994) *Plant J.*, 6, 861–877.
35. Van der Krol et al. (1990) *Plant Cell*, 2, 291–299.
36. Yamaya et al. (1988) *Mol. Gen. Genet.*, 215, 173–175.
37. Yamaya et al. (1988) *Mol. Gen. Genet.*, 211, 520–525.

Baulcombe et al. (1987) *Mol. Gen. Genet.*, 209, 33–40.
Baulcombe et al. (1995) *Plant J.*, 7, 1045–1053.
Bishop et al. (1996) *Plant Cell*, 8, 959–969.
Dawson et al. (1989) *Virology*, 172, 285–292.
Depicker et al. (1982) *J. Mol. Appl. Genet.*, 1, 561–573.
Dolja et al. (1992) *Proc. Natl. Acad. Sci. USA*, 89, 10208–10212.
Futterer, J. and Hohn. T. (1991) *EMBO J.*, 10, 3887–3896.
Hamilton et al. (1995) *Current Topics In Microbiology And Immunology*, 197, 77–89.
Jefferson et al. (1986) *Proc. Natl. Acad. Sci. USA*, 83, 8447–8451.
Jones et al. (1992) *Transgenic Res.*, 1, 285–297.
Kavanagh et al. (1992) *Virology*, 189, 609–617.
Matzke, M. A. and Matzke, A. J. M. (1993) *Annu. Rev. Plant Physiol. Plant. Mol. Biol.*, 44, 53–76.
Mori et al. (1993) *J. Gen. Virol.*, 74, 1255–1260.
Park et al. (1996) *Plant J.*, 9, 183–194.
Poulson et al. (1986) *Mol. Gen. Genet.*, 205, 193–200.
Sanders et al. (1987) *Nucleic Acids Res.*, 15, 1543–1558.
Scholthof et al. (1993), *Mol. Plant-Microbe Interact.*, 6, 309–322.
Sijen et al. (1996), *Plant Cell*, 8, 2277–2294.
Torii et al. (1996) *Plant Cell*, 8, 735–746.
Vaucheret, H. (1993) *C. R. Acad. Sci. Paris*, 316, 1471–1483.
Vaucheret, H. (1994) *C. R. Acad. Sci. Paris*, 317, 310–323.
Walker, J. C. (1993) *Plant J.*, 3, 451–456.
Ward et al. (1988) *EMBO J.*, 7, 1583–1587.
Ziegler-Graff et al. (1991) *Virology*, 182, 145–155.

What is claimed is:

1. A recombinant DNA construct comprising a promoter operably linked to DNA which can be transcribed in a plant cell to an RNA transcript, which RNA transcript comprises plant virus sequence from an RNA virus which confers on the RNA transcript the ability to replicate in the cytoplasm of the plant cell wherein the RNA transcript lacks all or part of the sequence of said virus not required for replication in the cytoplasm and wherein the RNA transcript comprises at least one targeting sequence which causes post-transcriptional gene silencing of at least one target gene, wherein the targeting sequence is a sequence foreign to the plant virus sequence, and is 23 nucleotides or longer.

2. The DNA construct as claimed in claim 1, wherein the targeting sequence shares greater than 80, 85, 90 or 95% homology with a target sequence in the target gene.

3. The DNA construct as claimed in claim 1, comprising a multiplicity of targeting sequences.

4. The DNA construct as claimed in claim 1, wherein said targeting sequence is included in the construct as an intact open reading frame such that it is transcribed from the RNA transcript as a subgenomic RNA.

5. The DNA construct as claimed in claim 1, wherein the target gene is selected from the group consisting of an endogenous plant gene, and a gene from a pathogen.

6. The DNA construct as claimed in claim 5, wherein the endogenous plant gene is one associated with at least one of the following traits, said trait being selected from the group consisting of ripening, pollen formation, lignin biosynthesis, flower pigment production, regulatory pathways controlling development, environmental responses, growth, disease resistance, and toxin production.

7. A method of increasing the resistance of a plant to a viral pathogen comprising the step of stably incorporating the construct of claim 1 within the genome of said plant, wherein the target gene is a gene of the viral pathogen, wherein expression of said RNA transcript, and replication of said RNA transcript, results in post-transcriptional gene silencing of said target gene and increased resistance of said plant to said viral pathogen.

8. The method as claimed in claim 7 where the target gene is involved in a process selected from the group consisting of replication of the pathogen and infectivity of the pathogen.

9. A recombinant Agrobacterium binary vector comprising a DNA construct comprising a promoter operably linked to DNA which can be transcribed in a plant cell to an RNA transcript, which RNA transcript comprises plant virus sequence from an RNA virus which confers on the RNA transcript the ability to replicate in the cytoplasm of the plant cell, said RNA transcript lacking all or part of the sequence of said virus not required for replication in the cytoplasm and wherein the RNA transcript comprises at least one targeting sequence which causes post-transcriptional gene silencing of a target gene wherein said at least one targeting sequence is a sequence foreign to the plant virus sequence and is 23 nucleotides or longer.

10. A plant comprising the vector of claim 9.

11. A plant host cell comprising a recombinant DNA construct comprising a promoter operably linked to DNA which can be transcribed in said plant cell to an RNA transcript, which RNA transcript comprises plant virus sequence from an RNA virus which confers on the RNA transcript the ability to replicate in the cytoplasm of the plant cell, said transcript lacking all or part of the sequence of said virus not required for replication in the cytoplasm and wherein the RNA transcript comprises at least one targeting sequence which causes post-transcriptional gene silencing of a target gene, wherein the targeting sequence is a sequence foreign to the plant virus sequence, and is 23 nucleotides or longer.

12. A method of down-regulating expression of a target gene in a plant including the step of introducing the vector of claim 9 into a plant cell such that said construct is stably incorporated into the genome of the cell and regenerating a plant from said plant cell, wherein expression of said RNA transcript, and replication of said RNA transcript, results in post-transcriptional gene silencing of said target gene.

13. A method of down-regulating expression of a target gene in a plant which comprises introducing the construct of claim 1 into a plant cell such that the construct is stably incorporated into the genome of the cell, and regenerating a plant from said plant cell, wherein expression of said RNA transcript, and replication of said RNA transcript, results in post-transcriptional gene silencing of said target gene.

14. The DNA construct as claimed in, claim 1, wherein the plant RNA virus is selected from the group consisting of potato virus X, tobacco mosaic virus, tobacco etch virus, tobacco rattle virus, tomato bushy stunt virus and brome mosaic virus.

15. The DNA construct as claimed in claim 1, wherein the promoter is constitutive.

16. The DNA construct as claimed in claim 1, wherein the promoter is selected from the group consisting of developmentally regulated promoters, inducible promoters, or tissue specific promoters.

17. The DNA construct as claimed in claim 1, wherein the promoter is selected from the group consisting of CaMV 35S, nos, and GST-II-27 gene.

18. The DNA construct as claimed in claim 1, further comprising a transcriptional terminator.

19. The DNA construct as claimed in claim 1, wherein the RNA transcript does not encode a coat protein of the plant virus from which the plant virus sequence is derived.

* * * * *